United States Patent
Hoffmann et al.

(10) Patent No.: US 7,282,469 B2
(45) Date of Patent: Oct. 16, 2007

(54) 4-TRIFLUOROMETHYLPYRAZOLYL-SUBSTITUTED PYRIDINES AND PYRIMIDINES

(75) Inventors: Michael Gerhard Hoffmann, Flörsheim (DE); Hendrik Helmke, Liederbach (DE); Lothar Willms, Hofheim (DE); Thomas Auler, Bad Soden (DE); Hermann Bieringer, Eppstein (DE); Hubert Menne, Hofheim (DE)

(73) Assignee: Bayer CropScience GmbH, Frankfurt (DE)

( * ) Notice: Subject to any disclaimer, the term of this patent is extended or adjusted under 35 U.S.C. 154(b) by 759 days.

(21) Appl. No.: 10/627,256

(22) Filed: Jul. 24, 2003

(65) Prior Publication Data

US 2004/0082475 A1 Apr. 29, 2004

(30) Foreign Application Priority Data

Jul. 25, 2002 (DE) .................. 102 34 876

(51) Int. Cl.
*C07D 401/14* (2006.01)
*C07D 403/14* (2006.01)
*A01N 43/56* (2006.01)

(52) U.S. Cl. ............... 504/242; 504/250; 504/253; 544/320; 544/321; 546/256; 546/275.4

(58) Field of Classification Search ............... 544/320, 544/321; 546/256, 275.4; 504/242, 250, 504/253

See application file for complete search history.

(56) References Cited

FOREIGN PATENT DOCUMENTS

| EP | 1 101 764 A1 | 5/2001 |
|---|---|---|
| WO | WO-98/40379 | 9/1998 |
| WO | WO-99/28301 | 6/1999 |
| WO | WO-03/016308 A1 | 2/2003 |

OTHER PUBLICATIONS

Maier et al., CAPLUS Abstract 134:366871, 2001.*

* cited by examiner

*Primary Examiner*—Deepak Rao
(74) *Attorney, Agent, or Firm*—Connolly Bove Lodge & Hutz LLP

(57) ABSTRACT

A description is given of 4-trifluoromethylpyrazolyl-substituted pyridines and pyrimidines of the formula (I) and of their use as herbicides.

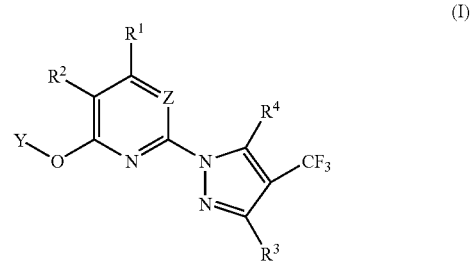

In this formula (I), $R^1$, $R^2$, $R^3$ and $R^4$ stand for various radicals, A for an aromatic or heteroaromatic radical, and Z denotes a nitrogen or carbon atom.

14 Claims, No Drawings

4-TRIFLUOROMETHYLPYRAZOLYL-SUBSTITUTED PYRIDINES AND PYRIMIDINES

The invention pertains to the technical field of herbicides, particularly that of herbicides from the class of the heteroaryl-pyrazoles, for selectively controlling broadleaf and gramineous weeds in crops of useful plants.

From a variety of publications it is already known that certain pyridines and pyrimidines substituted by azol radicals, such as pyrazolyl, imidazolyl and triazolyl, possess herbicidal properties. For instance, WO 99/28301 discloses pyridines and pyrimidines which carry an azol radical in position 2 and, in position 6, an aromatic or heteroaromatic radical attached via a carbon atom. WO 98/40379 describes pyridines and pyrimidines which carry in position 2 an azol radical and, in position 6, an aromatic or heteroaromatic radical attached via an oxygen, nitrogen or sulfur atom. The azol radical in position 2 can be substituted by a variety of radicals. That publication discloses various substituents for the pyrazolyl radical, all of which are in position 3. EP-A 1 101 764 describes herbicidal 4-methylpyridines substituted in position 2 by 3-trifluoromethyl-1-pyazolyl.

The compounds known from these publications, however, frequently exhibit a herbicidal activity which is inadequate. It is an object of the present invention, therefore, to provide herbicidally effective compounds having herbicidal properties which are improved over those of the prior art compounds.

It has now been found that certain 4-trifluoromethylpyrazolyl-substituted pyridines and pyrimidines are especially suitable herbicides. The present invention accordingly first provides compounds of the formula (I), their N-oxides, and their salts,

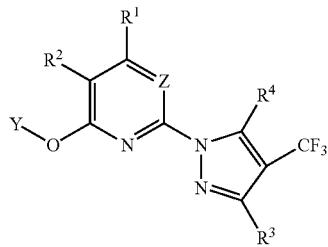

(I)

in which the radicals and indices have the following definitions:

Z is N or $CR^8$;
Y is a radical from the group Y1 to Y7:

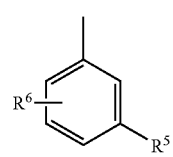

Y1

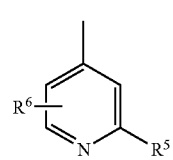

Y2

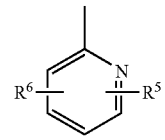

Y3

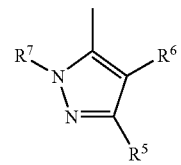

Y4

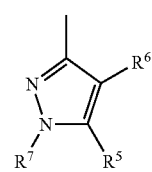

Y5

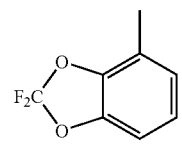

Y6

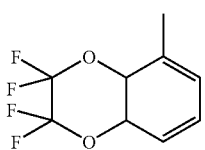

Y7

$R^1$ and $R^2$ independently are each hydrogen, halogen, cyano, isocyano, OH, $COOR^{10}$, $COR^{10}$, $CH_2OH$, $CH_2SH$, $CH_2NH_2$, $NO_2$, $CSNH_2$, $CONH_2$, $(C_1-C_4)$-alkyl, halo-$(C_1-C_4)$-alkyl, $(C_3-C_6)$-cycloalkyl, $(C_1-C_4)$-alkoxy, halo-$(C_1-C_4)$-alkoxy, $(C_1-C_2)$-alkoxy-$(C_1-C_2)$-alkyl, $(C_2-C_4)$-alkenyl, $(C_2-C_4)$-alkynyl, $(C_3-C_4)$-alkenyloxy, $(C_3-C_4)$-alkynyloxy, $(C_1-C_2)$-alkylthio-$(C_1-C_2)$-alkyl, $S(O)_nR^9$, $(C_1-C_2)$-alkylsulfonyl-$(C_1-C_2)$-alkyl, amino, $(C_1-C_4)$-alkylamino, $(C_1-C_3)$-alkylcarbonylamino, $(C_1-C_4)$-alkylsulfonylamino, $(C_1-C_4)$-alkylsulfonylamino, or di-$(C_1-C_4)$-alkylamino;
$R^3$ and $R^4$ independently are each hydrogen, halogen, cyano, $(C_1-C_4)$-alkyl, halo-$(C_1-C_4)$-alkyl, $(C_1-C_4)$-alkoxy or halo-$(C_1-C_4)$-alkoxy;
$R^5$ is halogen, cyano, $(C_1-C_4)$-alkyl, halo-$(C_1-C_4)$-alkyl, $(C_1-C_4)$-alkoxy, halo-$(C_1-C_4)$-alkoxy, halo-$(C_1-C_4)$-alkylthio, $(C_3-C_5)$-cycloalkyl, halo-$(C_3-C_5)$-cycloalkyl, $SF_5$, $S(O)_nR^9$, $(C_2-C_4)$-alkenyl or $(C_2-C_4)$-alkynyl;
$R^6$ is hydrogen, halogen, cyano, $(C_1-C_4)$-alkyl, halo-$(C_1-C_4)$-alkyl, $(C_1-C_4)$-alkoxy, halo-$(C_1-C_4)$-alkoxy or $S(O)_nR^9$;
$R^7$ is $(C_1-C_4)$-alkyl;
$R^8$ is hydrogen, halogen, cyano, $NO_2$, $(C_1-C_4)$-alkyl, $(C_1-C_4)$-alkoxy, hydroxy, amino, $(C_1-C_4)$-alkylamino, $(C_1-C_3)$-alkylcarbonylamino, $(C_1-C_4)$-alkylsulfonylamino, di-$(C_1-C_4)$-alkylamino or $S(O)_nR^9$;
$R^9$ is hydrogen, $(C_1-C_4)$-alkyl or halo-$(C_1-C_4)$-alkyl;
$R^{10}$ is hydrogen or $(C_1-C_4)$-alkyl;
n is 0, 1 or 2.

In formula (I) and all subsequent formulae alkyl, alkenyl, and alkynyl radicals having more than two or three carbon atoms respectively can be straight-chain or branched. Alkyl radicals are methyl, ethyl, n- or i-propyl, n-, i-, t- or 2-butyl. Alkenyl accordingly is ethenyl, 1-propenyl, 2-propenyl, and the various butenyl isomers. Alkynyl is ethynyl, 1-propynyl, 2-propynyl, and the various butynyl isomers. The terms in their composite definitions such as alkoxy, alkenyloxy, alkynyloxy and alkylthio are to be understood analogously. Thus alkynyloxy, for example, stands for HC≡CCH$_2$O, CH$_3$C≡CCH$_2$O and CH$_3$C≡CCH$_2$CH$_2$O.

Cycloalkyl is cyclopropyl, cyclobutyl, cyclopentyl or cyclohexyl.

In the case of a doubly substituted amino group, such as dialkylamino, these two substituents can be identical or different.

Halogen is fluorine, chlorine, bromine or iodine. Haloalkyl is alkyl substituted wholly or partly by halogen, preferably by fluorine, chlorine and/or bromine, in particular by fluorine or chlorine, e.g. CF$_3$, CHF$_2$, CH$_2$F, CF$_3$CF$_2$, CH$_2$FCHCl, CCl$_3$, CHCl$_2$, CH$_2$CH$_2$Cl; haloalkoxy is for example OCF$_3$, OCHF$_2$, OCH$_2$F, CF$_3$CF$_2$O, OCH$_2$CF$_3$ and OCH$_2$CH$_2$Cl; similar comments apply to other halogen-substituted radicals.

Depending on the nature and linking of the substituents the compounds of the formula (I) can exist as stereoisomers. Where, for example, there is a double bond, diastereomers may occur. Where, for example, there are one or more asymmetric carbon atoms, enantiomers and diastereomers may occur. Stereoisomers can be obtained from the as-prepared mixtures by standard separation methods, e.g. by chromatographic separation techniques. Likewise, stereoisomers may be prepared selectively using stereoselective reactions and optically active starting materials and/or auxiliaries. The invention also relates to all of the stereoisomers and mixtures thereof which, while embraced by the formula (I), have not been specifically defined.

Compounds of the formula (I) can in principle form N-oxides. N-Oxides can be prepared in accordance with methods known to the skilled worker, by reaction with oxidizing reagents, such as peracids, hydrogen peroxide, and sodium perborate. Such methods are described for example in T. L. Gilchrist, Comprehensive Organic Synthesis, Volume 7, pages 748 to 750, S. V. Ley, Ed., Pergamon Press.

Compounds of the formula (I) can in principle form salts by addition with
a) acids, such as hydrogen chloride, hydrogen bromide, nitric acid, phosphoric acid, sulfuric acid, acidic acid, oxalic acid, or
b) bases, such as pyridine, ammonia, triethylamine, sodium carbonate, potassium carbonate, sodium hydroxide, potassium hydroxide.

Preferred embodiments of the compounds of the invention always include the N-oxides and salts, unless noted otherwise below.

Of particular interest are compounds of the formula (I) in which Y is a radical from the group Y1 to Y6.

Compounds of the formula (I) which have been found advantageous include those wherein
$R^1$ and $R^2$ independently are each hydrogen, halogen, cyano, OH, CHO, vinyl, (C$_1$-C$_4$)-alkyl, halo-(C$_1$-C$_4$)-alkyl, vinyl or (C$_1$-C$_4$)-alkoxy, and the other substituents and indices are each as defined earlier on above.

Likewise of advantage are compounds of the formula (I), wherein
$R^3$ and $R^4$ independently are each hydrogen, halogen, methyl or methoxy, and the other substituents and indices are each as defined earlier on above.

Preferred compounds of the formula (I) are those wherein
$R^1$ is hydrogen, halogen, cyano, CHO, methoxy, methyl or ethyl, and
$R^2$ is hydrogen, OH, methyl, ethyl, methoxy or ethoxy, and the other substituents and indices are each as defined earlier on above.

Preference is also given to compounds of the formula (I), wherein $R^3$ and $R^4$ are each hydrogen or methyl, and the other substituents and indices are each as defined earlier on above.

Particular preference is given to compounds of the formula (I), wherein $R^8$ is hydrogen, halogen or (C$_1$-C$_4$)-alkyl, and the others substituents and indices are each as defined earlier on above.

Likewise particularly preferred are compounds of the formula (I), wherein $R^5$ is halogen, cyano, halo-(C$_1$-C$_4$)-alkyl, halo-(C$_1$-C$_4$)-alkoxy or halo-(C$_1$-C$_4$)-alkylthio, and the other substituents and indices are each as defined earlier on above.

Also of particular preference are compounds of the formula (I), wherein $R^6$ is hydrogen, and the other substituents and indices are each as defined earlier on above.

In all formulae below, the substituents and symbols have the same definition as described under formula (I), unless otherwise defined.

Compounds of the invention can be prepared, for example, by the reaction pathways indicated in the schemes below:

In accordance with scheme 1 compounds of the formula (IIa) in which $E^1$ is a leaving group, such as halogen, methylsulfonyl or tosyl, can be reacted under base catalysis with a compound of the formula (III). Such reactions are known to the skilled worker.

Scheme 1:

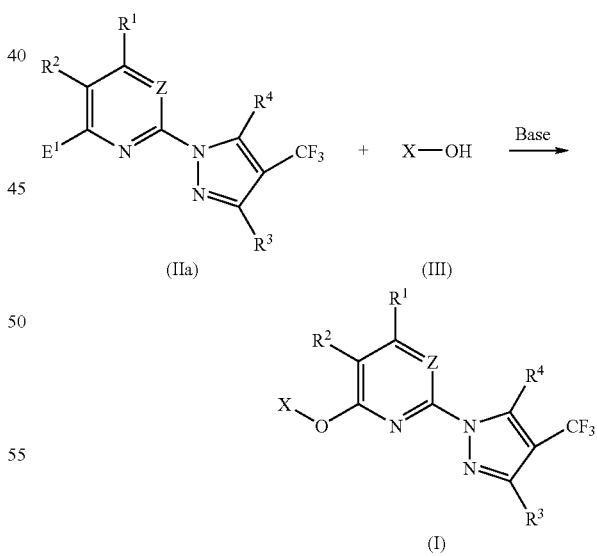

Compounds of the formula (IIa) in which $E^1$ is halogen can be prepared, for example, in accordance with scheme 2 under base catalysis from a compound of the formula (IV) with a pyrazole of the formula (V). In this reaction the regioisomers (IIa) and (IIb) may form, and can be separated, for example, by chromatographic workup. Such reactions are known to the skilled worker.

Scheme 2:

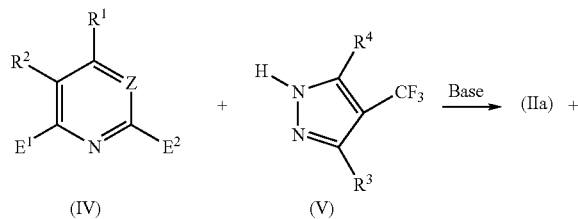

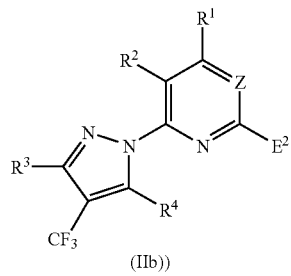

Compounds of the formula (IIa) in which $E^1$ is methylsulfonyl can be prepared, for example, in accordance with scheme 3 by oxidation with m-chloroperbenzoic acid (MCPA) or Oxone® forming a compound of the formula (IIc). Such reactions are known to the skilled worker from, for example, J. March, Advanced Organic Chemistry, John Wiley, New York, 1992, 4$^{th}$ Ed., pages 1201 to 1203.

Scheme 3:

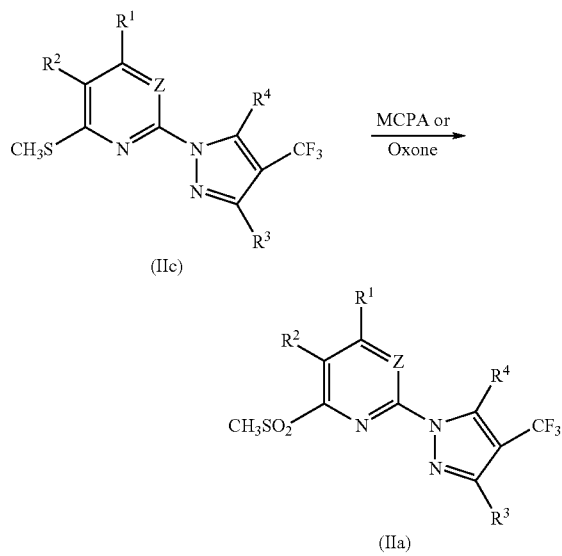

Compounds of the formula (IIb) can be prepared, for example, in accordance with scheme 4 by base-catalyzed reaction of a compound of the formula (VI) with the pyrazole (V). Suitable bases are the carbonates of potassium and sodium, the hydroxides of potassium and sodium, and also sodium hydride. Appropriately these reactions are conducted in solvents such as dimethylformamide, dioxane, THF, sulfolane and acetonitrile. Such reactions are known to the skilled worker.

Scheme 4:

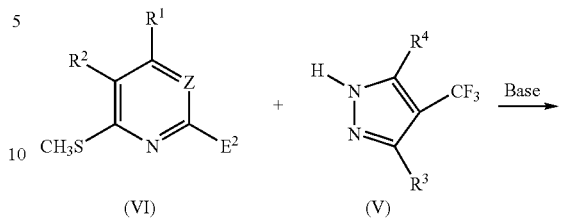

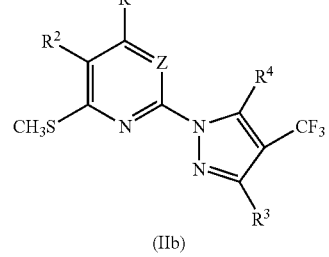

Compounds of the formula (VI) can be prepared, for example, from compounds of the formula (IV) in which $E^1$ and $E^2$ are each halogen by reaction with a sodium salt or potassium salt of methyl mercaptane in tetrahydrofurane or dioxane. Such reactions are known to the skilled worker.

Compounds of the formula (IV) in which $E^1$ and $E^2$ are each halogen are either available commercially or can be prepared in accordance with methods known to the skilled worker. Such methods known to the skilled worker are described for example in Advances in Heterocyclic Chemistry, Katritzky, A. R., Ed., Academic Press, New York, 1993, Volume 58, pages 301 to 305; Heterocyclic Compounds, Elderfield, R. C., Ed., John Wiley, New York, 1957, Volume 6, pages 265 to 270.

Pyrazoles of the formula (V) can be prepared in accordance with the methods known to the skilled worker. The preparation of 4-trifluoromethylpyrazole is described for example in THL, 37, 11, 1996, pages 1829-1832.

The compounds of the formula (I) according to the invention have an excellent herbicidal activity against a broad range of economically important monocotyledonous and dicotyledonous weed plants. The active substances control perennial weeds equally well which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the perennial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennials. Harmful plants which are found under the specific culture conditions of rice, such as, for example, *Echinochloa, Sagittaria, Alisma, Eleocharis, Scirpus* and *Cyperus*, are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that competition by the weeds, which is detrimental for the crop plants, is thus eliminated at a very early stage and in a sustained manner. In particular, the compounds according to the invention have an outstanding action against *Amaranthus retroflexus, Avena* sp., *Echinochloa* sp., *Cyperus serotinus, Lolium multiflorum, Setaria viridis, Sagittaria pygmaea, Scirpus juncoides, Sinapis* sp. and *Stellaria media*.

Although the compounds according to the invention have an outstanding herbicidal activity against monocotyledonous and dicotyledonous weeds, crop plants of economically important crops such as, for example, wheat, barley, rye, rice, maize, sugar beet, cotton and soya only suffer negligible damage, if any. In particular, they are outstandingly well tolerated in wheat, barley, maize, rice and soybean. This is why the present compounds are highly suitable for the selective control of unwanted vegetation in stands of agricultural crop plants or ornamentals.

Owing to their herbicidal properties, the active substances can also be employed for controlling weed plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, storage properties, composition and specific constituents. Thus, transgenic plants are known which have an increased starch content or whose starch quality has been modified, or those whose fatty acid composition in the harvested material is different.

The compounds of the formula (I) according to the invention or their salts are preferably employed in economically important transgenic crops of useful plants and ornamentals, for example cereals such as wheat, barley, rye, oats, millet, rice, cassava and maize, or else crops of sugar beet, cotton, soya, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, a number of cases of the following have been described:

recombinant modifications of crop plants for the purposes of modifying the starch synthesized in the plants (for example WO 92/11376, WO 92/14827, WO 91/19806), transgenic crop plants which exhibit resistances to certain herbicides of the glufosinate type (cf. eg. EP-A-0242236, EP-A-242246), glyphosate type (WO 92/00377) or of the sulfonylurea type (EP-A-0257993, U.S. Pat. No. 5,013,659), transgenic crop plants, for example cotton, with the ability to produce *Bacillus thuringiensis* toxins (*Bt* toxins), which make the plants resistant to certain pests (EP-A-0142924, EP-A-0193259), transgenic crop plants with a modified fatty acid spectrum (WO 91/13972).

A large number of techniques in molecular biology, with the aid of which novel transgenic plants with modified properties can be generated, are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423-431.

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves transcripts of the abovementioned gene product.

To this end it is possible, on the one hand, to use DNA molecules which encompass all of the coding sequence of a gene product including any flanking sequences which may be present, but also DNA molecules which only encompass portions of the coding sequence, it being necessary for these portions to be long enough to cause an antisense effect in the cells. Another possibility is the use of DNA sequences which have a high degree of homology with the coding sequences of a gene product, but are not completely identical.

In the expression of nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants can be plants of any desired plant species, i.e., both monocotyledonous and dicotyledonous plants.

Thus, transgenic plants can be obtained which exhibit modified properties owing to the overexpression, suppression or inhibition of homologous (i.e., natural) genes or gene sequences or expression of heterologous (i.e., foreign) genes or gene sequences.

When using the active substances according to the invention in transgenic crops, effects are frequently observed in addition to the effects against harmful plants to be observed in other crops, which are specific for the application in the transgenic crop in question, for example a modified or specifically widened weed spectrum which can be controlled, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling weed plants in transgenic crop plants.

The substances according to the invention additionally have outstanding growth-regulatory properties in crop plants. They intervene in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops, allowing lodging to be reduced or prevented completely.

The compounds according to the invention can be employed in the form of wettable powders, emulsifiable concentrates, sprayable solutions, dusts or granules in the customary preparations. The invention therefore furthermore relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Kuchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, such as butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays, such as kaolin, bentonite and pyrophyllite, or diatomaceous earth.

Suspension concentrates can be water based or oil based. They can be prepared for example by wet grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants, as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules see, for example, methods in "Spray-Drying Handbook" 3rd Ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8-57.

For further details on the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the tackifiers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances, such as, for example, insecticides, acaricides, herbicides, fungicides, and with safeners, fertilizers and/or growth regulators, for example in the form of a readymix or a tank mix.

Active substances which can be employed in combination with the active substances according to the invention in mixture formulations or in the tank mix are, for example, known active substances as are described, for example, in Weed Research 26, 441-445 (1986) or "The Pesticide Manual", 11th edition, The British Crop Protection Council and the Royal Soc. of Chemistry, 1997 and literature cited therein. Known herbicides which may be mentioned, and can be combined with the compounds of the formula (I), are, for example, the following active substances (note: the compounds are either designated by the common name according to the International Organization for Standardization (ISO) or using the chemical name, if appropriate together with a customary code number): acetochlor; acifluorfen; aclonifen; AKH 7088, i.e. [[[1-[5-[2-chloro-4-(trifluoromethyl) -phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDM, i.e. 2-chloro-N,N -di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; diallate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl) -5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F -6285); sulfazuron; sulfometuron-methyl; sulfosate (ICI-A0224);

TCA; tebutam (GCP -5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; K1H-9201; ET-751; K1H-6127 and K1H-2023.

For use, the formulations, which are present in commercially available form, are diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use. The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

Preparation of 5-methyl-4-(3-trifluoromethylphenoxy)-2-(4-trifluoromethyl-1H-1-pyrazolyl)pyrimidine A mixture of 11.2 g (36.4 mmol) of 5-methyl-4-methylsulfonyl-2-(4-trifluoromethyl-1H -1-pyrazolyl)pyrimidine, 7.7 g (47.4 mmol) of 3-trifluoromethylphenol and 10.1 g (72.9 mmol) of $K_2CO_3$ in 200 ml of DMF is stirred at RT for 24 h. It is then poured into 200 ml of water and extracted with four times 100 ml of $CH_2Cl_2$. The combined organic phase is dried over $Na_2SO_4$, filtered and concentrated. Chromatographic purification on silica gel with heptane/ethyl acetate (1:1) as eluent gives 10.2 g (72%) of 5-methyl-4-(3-trifluoromethylphenoxy)-2-(4-trifluoromethyl-1H-1-pyrazolyl)pyrimidine as colourless crystals having a melting point of 103-105° C.

$^1$H-NMR: δ [$CDCl_3$] 2.40 (s, 3H), 7.45 (m, 1H), 7.55 (s, 1H), 7.62 (m, 2H), 7.92 (s, 1H), 8.33 (s, 1H), 8.52 (s, 1H).

Preparation of 5-methyl-2-(4-trifluoromethyl)-1H-1-pyrazolyl-4-(2-trifluoromethyl-4-pyridyloxy)pyrimidine A mixture of 0.38 g (1.23 mmol) of 5-methyl-4-methylsulfonyl-2-(4-trifluoromethyl-1H -1-pyrazolyl)pyrimidine, 0.2 g (1.23 mmol) of 2-trifluoromethyl-4-hydroxypyridine and 0.33 g (2.45 mmol) of $K_2CO_3$ in 10 ml of DMF is stirred at 60° C. for 6 h and then at RT for 48 h. It is then poured into 20 ml of water and extracted with four times 15 ml of $CH_2Cl_2$. The combined organic phase is dried over $Na_2SO_4$, filtered and concentrated. Chromatographic purification on silica gel using heptane/ethyl acetate (3:7) as eluent gives 0.16 g (33%) of 5-methyl-2-(4-trifluoromethyl)-1H-1-pyrazolyl-4-(2-trifluoromethyl-4-pyridyloxy)pyrimidine as a pale yellow oil.

$^1$H-NMR: δ [$CDCl_3$] 2.40 (s, 3H), 7.50 (dd, 1H), 7.70 (d, 1H), 7.95 (s, 1H), 8.50 (s, 1H), 8.60 (s, 1H), 8.85 (d, 1H).

Preparation of 2-(1-methyl-3-trifluoromethylpyrazol-5-yloxy)-6-(4-trifluoromethylpyrazol-1-yl)pyridine 0.262 g of 4-trifluoromethylpyrazole is introduced under nitrogen in 7 ml of dimethylacetamide and at 0° C. 0.057 g of NaH is added. The mixture is allowed to come to RT over 30 min and then 0.5 g of 2-fluoro-6-(1-methyl-3-trifluoromethylpyrazol-5-yloxy)pyridine is added and the mixture is heated at 140° C. for 7 h, cooled to RT and poured into water. The product is extracted twice with ethyl acetate/heptane (1:1), washed with water and saturated sodium chloride solution, dried over $MgSO_4$ and concentrated. Chromatographic purification on silica gel gives 0.349 g of 2-(1-methyl-3-trifluoromethylpyrazol-5-yloxy)-6-(4-trifluoromethylpyrazol-1-yl)pyridine as white crystals.

$^1$H-NMR: δ [$CDCl_3$] 3.82 (s, 3H), 6.34 (s, 1H), 7.00 (d, 1H), 7.82 (d, 1H), 7.88 (s, 1H), 7.97 (t, 1H), 8.43 (s, 1H).

Preparation of 4-methyl-2-(1-methyl-3-trifluoromethylpyrazol-5-yloxy)-6-(4-trifluoromethylpyrazol-1-yl)pyridine 0.385 g of 4-trifluoromethylpyrazole is introduced under nitrogen in 10 ml of dimethylacetamide and at 0° C. 0.096 g of NaH is added. The mixture is allowed to come to RT over 30 min and then 0.757 g of 2-chloro-4-methyl-6-(1-methyl-3-trifluoromethylpyrazol-5-yloxy)pyridine is added and the mixture is heated at 140° C. for 7 h, cooled to RT and poured into water. The product is extracted twice with ethyl acetate/heptane (1:1) and twice with ethyl acetate and then washed with water and saturated sodium chloride solution, dried over $MgSO_4$ and concentrated. Chromatographic purification on silica gel gives 0.332 g of 4-methyl-2-(1-methyl-3-trifluoromethylpyrazol-5-yloxy)-6-(4-trifluoromethylpyrazol-1-yl)pyridine as white crystals.

$^1$H-NMR: δ [$CDCl_3$] 2.50 (s, 3H), 3.82 (s, 3H), 6.30 (s, 1H), 6.82 (d, 1H), 7.67 (s, 1H), 7.86 (s, 1H), 8.43 (s, 1H).

Preparation of 4-methoxy-2-(1-methyl-3-trifluoromethylpyrazol-5-yloxy)-6-(4-trifluoromethylpyrazol-1-yl)pyridine 0.068 g of 4-trifluoromethylpyrazole is introduced under nitrogen in 5 ml of dimethylacetamide and at 0° C. 0.017 g of NaH is added. The mixture is allowed to come to RT over 30 min and then 0.2 g of 4-methoxy-2,6-bis(1-methyl-3-trifluoromethylpyrazol-5-yloxy)pyridine is added and the mixture is heated at 135° C. for 5 h, cooled to RT and poured into water. The product is extracted three times with ethyl actate/heptane (1:1), washed with water and saturated sodium chloride solution, dried over $MgSO_4$ and concentrated.

Chromatographic purification on silica gel gives 0.036 g of 4-methoxy-2-(1-methyl-3-trifluoromethylpyrazol-5-yloxy)-6-(4-trifluoromethylpyrazol-1-yl)pyridine as a wax-like substance.

$^1$H-NMR: δ [$CDCl_3$] 3.81 (s, 3H), 3.99 (s, 3H), 6.29 (s, 1H), 6.44 (d, 1H), 7.40 (d, 1H), 7.85 (s, 1H), 8.42 (s, 1H).

The examples listed in the tables below were prepared in analogy to methods specified above or are obtainable in analogy to the methods specified above.

The abbreviations used here have the following definitions:

TABLE 1

Compounds of the formula (I) according to the invention in which the substituents and symbols are defined as follows:
Y = Y1        R⁶ = H

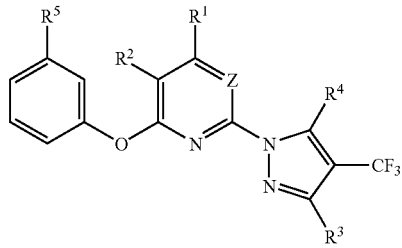

| No. | R⁵ | R² | R¹ | R³ | R⁴ | Z | Physical data |
|---|---|---|---|---|---|---|---|
| 1.1 | H | H | H | H | CF₃ | N | ¹H-NMR (CDLC₃): 6.90(d, 1H); 7.45 (m, 1H); 7.55(m, 1H); 7.62(m, 2H); 7.98(s, 1H); 8.50(s, 1H); 8.70(d, 1H) |
| 1.2 | H | H | H | H | CF₃ | CH | m.p. 55–56° C. |
| 1.3 | H | H | H | H | CF₃ | CMe | |
| 1.4 | H | H | H | H | CF₃ | CCl | |
| 1.5 | H | H | Me | H | CF₃ | CH | |
| 1.6 | H | OH | H | Me | CF₃ | CH | |
| 1.7 | H | Me | H | H | CF₃ | N | m.p. 103–105° C. |
| 1.8 | H | OMe | H | H | CF₃ | CH | |
| 1.9 | H | H | H | H | Cl | N | |
| 1.10 | H | H | H | H | Cl | CH | |
| 1.11 | H | H | H | H | Cl | CMe | |
| 1.12 | H | H | H | H | Cl | CCl | |
| 1.13 | H | H | Me | H | Cl | OH | |
| 1.14 | H | OH | H | Me | Cl | CH | |
| 1.15 | H | Me | H | H | Cl | CH | |
| 1.16 | H | OMe | H | H | Cl | CH | |
| 1.17 | H | H | H | H | CN | N | |
| 1.18 | H | H | H | H | CN | CH | m.p. 86–88° C. |
| 1.19 | H | H | H | H | CN | CMe | |
| 1.20 | H | H | H | H | CN | CCl | |
| 1.21 | H | H | Me | H | CN | CH | |
| 1.22 | H | CH | H | Me | CN | CH | |
| 1.23 | H | Me | H | H | CN | CH | |
| 1.24 | H | OMe | H | H | CN | CH | |
| 1.25 | H | H | H | H | OCF₂H | N | |
| 1.26 | H | H | H | H | OCF₂H | CH | |
| 1.27 | H | H | H | H | OCF₂H | OMe | |
| 1.28 | H | H | H | H | OCF₂H | CCl | |
| 1.29 | H | H | Me | H | OCF₂H | CH | |
| 1.30 | H | CH | H | Me | OCF₂H | CH | |
| 1.31 | H | Me | H | H | OCF₂H | CH | |
| 1.32 | H | OMe | H | H | OCF₂H | CH | |
| 1.33 | H | H | H | H | CN | N | |
| 1.34 | H | H | H | H | CN | CH | |
| 1.35 | H | H | H | H | CN | OMe | |
| 1.36 | H | H | H | H | CN | 001 | |
| 1.37 | H | H | Me | H | CN | CH | |
| 1.38 | H | OH | H | Me | CN | CH | |
| 1.39 | H | Me | H | H | CN | CH | |
| 1.40 | H | OMe | H | H | CN | CH | |
| 1.41 | H | H | H | H | CN | N | |
| 1.42 | H | H | H | H | CN | CH | |
| 1.43 | H | H | H | H | CN | OMe | |
| 1.44 | H | H | H | H | CN | CCl | |
| 1.45 | H | H | Me | H | CN | CH | |
| 1.46 | H | OH | H | Me | CN | CH | |
| 1.47 | H | Me | H | H | CN | CH | |
| 1.48 | H | OMe | H | H | CN | CH | |
| 1.49 | Me | H | H | H | CF₃ | N | m.p. 109–111° C. |
| 1.50 | Me | H | H | H | CF₃ | CH | |
| 1.51 | Me | H | H | H | CF₃ | OMe | |
| 1.52 | Me | H | H | H | CF₃ | CCl | |
| 1.53 | Me | H | Me | H | CF₃ | CH | |
| 1.54 | Me | OH | H | Me | CF₃ | CH | |
| 1.55 | Me | Me | H | H | CF₃ | CH | |
| 1.56 | Me | OMe | H | H | CF₃ | CH | |
| 1.57 | Me | H | H | H | Cl | N | |
| 1.58 | Me | H | H | H | Cl | CH | |
| 1.59 | Me | H | H | H | Cl | CMe | |

TABLE 1-continued

Compounds of the formula (I) according to the invention in which the substituents and symbols are defined as follows:
Y = Y1   R⁶ = H

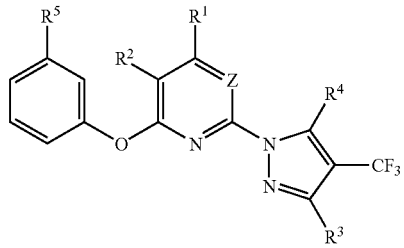

| | $R^5$ | $R^2$ | $R^1$ | $R^3$ | $R^4$ | Z |
|---|---|---|---|---|---|---|
| 1.60 | Me | H | H | H | Cl | CCl |
| 1.61 | Me | H | Me | H | Cl | CH |
| 1.62 | Me | CH | H | Me | Cl | CH |
| 1.63 | Me | Me | H | H | Cl | CH |
| 1.64 | Me | OMe | H | H | Cl | CH |
| 1.65 | Me | H | H | H | CN | N |
| 1.66 | Me | H | H | H | CN | CH |
| 1.67 | Me | H | H | H | CN | CMe |
| 1.68 | Me | H | H | H | CN | CCl |
| 1.69 | Me | H | Me | H | CN | CH |
| 1.70 | Me | OH | H | Me | CN | CH |
| 1.71 | Me | Me | H | H | CN | CH |
| 1.72 | Me | OMe | H | H | CN | CH |
| 1.73 | Me | H | H | H | OCF$_2$H | N |
| 1.74 | Me | H | H | H | OCF$_2$H | CH |
| 1.75 | Me | H | H | H | OCF$_2$H | CMe |
| 1.76 | Me | H | H | H | OCF$_2$H | CCl |
| 1.77 | Me | H | Me | H | OCF$_2$H | CH |
| 1.78 | Me | OH | H | Me | OCF$_2$H | CH |
| 1.79 | Me | Me | H | H | OCF$_2$H | CH |
| 1.80 | Me | OMe | H | H | OCF$_2$H | CH |
| 1.81 | Me | H | H | H | CN | N |
| 1.82 | Me | H | H | H | CN | CH |
| 1.83 | Me | H | H | H | CN | OMe |
| 1.84 | Me | H | H | H | CN | CCl |
| 1.85 | Me | H | Me | H | CN | CH |
| 1.86 | Me | OH | H | Me | CN | CH |
| 1.87 | Me | Me | H | H | CN | CH |
| 1.88 | Me | OMe | H | H | CN | CH |
| 1.89 | Me | H | H | H | CN | N |
| 1.90 | Me | H | H | H | CN | CH |
| 1.91 | Me | H | H | H | CN | CMe |
| 1.92 | Me | H | H | H | CN | CCl |
| 1.93 | Me | H | Me | H | CN | CH |
| 1.94 | Me | OH | H | Me | CN | CH |
| 1.95 | Me | Me | H | H | CN | CH |
| 1.96 | Me | OMe | H | H | CN | CH |
| 1.97 | CN | H | H | H | CF$_3$ | N |
| 1.98 | CN | H | H | H | CF$_3$ | CH |
| 1.99 | CN | H | H | H | CF$_3$ | CMe |
| 1.100 | CN | H | H | H | CF$_3$ | CCl |
| 1.101 | CN | H | Me | H | CF$_3$ | CH |
| 1.102 | CN | OH | H | Me | CF$_3$ | CH |
| 1.103 | CN | Me | H | H | CF$_3$ | CH |
| 1.104 | CN | OMe | H | H | CF$_3$ | CH |
| 1.105 | CN | H | H | H | Cl | N |
| 1.106 | CN | H | H | H | Cl | CH |
| 1.107 | CN | H | H | H | Cl | CMe |
| 1.108 | CN | H | H | H | Cl | CCl |
| 1.109 | CN | H | Me | H | Cl | CH |
| 1.110 | CN | OH | H | Me | Cl | CH |
| 1.111 | CN | Me | H | H | Cl | CH |
| 1.112 | CN | OMe | H | H | Cl | CH |
| 1.113 | CN | H | H | H | CN | N |
| 1.114 | CN | H | H | H | CN | CH |
| 1.115 | CN | H | H | H | CN | CMe |
| 1.116 | CN | H | H | H | CN | CCl |
| 1.117 | CN | H | Me | H | CN | CH |
| 1.118 | CN | OH | H | Me | CN | CH |
| 1.119 | CN | Me | H | H | CN | CH |
| 1.120 | CN | OMe | H | H | CN | CH |
| 1.121 | CN | H | H | H | OCF$_2$H | N |

TABLE 1-continued

Compounds of the formula (I) according to the invention in which the substituents and symbols are defined as follows:
Y = Y1    R⁶ = H

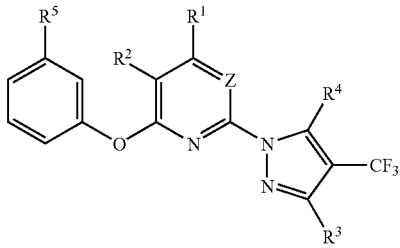

| | R⁵ | R² | R¹ | R⁶ | R⁴ | Z |
|---|---|---|---|---|---|---|
| 1.122 | CN | H | H | H | OCF₂H | CH |
| 1.123 | CN | H | H | H | OCF₂H | CMe |
| 1.124 | CN | H | H | H | OCF₂H | CCl |
| 1.125 | CN | H | Me | H | OCF₂H | CH |
| 1.126 | CN | CH | H | Me | OCF₂H | CH |
| 1.127 | CN | Me | H | H | OCF₂H | CH |
| 1.128 | CN | OMe | H | H | OCF₂H | CH |
| 1.129 | CN | H | H | H | CN | N |
| 1.130 | CN | H | H | H | CN | CH |
| 1.131 | CN | H | H | H | CN | CMe |
| 1.132 | CN | H | H | H | CN | CCl |
| 1.133 | CN | H | Me | H | CN | CH |
| 1.134 | CN | OH | H | Me | CN | CH |
| 1.135 | CN | Me | H | H | CN | CH |
| 1.136 | CN | OMe | H | H | CN | CH |
| 1.137 | CN | H | H | H | CN | N |
| 1.138 | CN | H | H | H | CN | CH |
| 1.139 | CN | H | H | H | CN | CMe |
| 1.140 | CN | H | H | H | CN | CCl |
| 1.141 | CN | H | Me | H | CN | CH |
| 1.142 | CN | OH | H | Me | CN | CH |
| 1.143 | CN | Me | H | H | CN | CH |
| 1.144 | CN | OMe | H | H | CN | CH |
| 1.145 | OMe | H | H | H | CF₃ | N |
| 1.146 | OMe | H | H | H | CF₃ | CH |
| 1.147 | OMe | H | H | H | CF₃ | CMe |
| 1.148 | OMe | H | H | H | CF₃ | CCl |
| 1.149 | OMe | H | Me | H | CF₃ | CH |
| 1.150 | OMe | OH | H | Me | CF₃ | CH |
| 1.151 | OMe | Me | H | H | CF₃ | CH |
| 1.152 | OMe | OMe | H | H | CF₃ | CH |
| 1.153 | OMe | H | H | H | Cl | N |
| 1.154 | OMe | H | H | H | Cl | CH |
| 1.155 | OMe | H | H | H | Cl | CMe |
| 1.156 | OMe | H | H | H | Cl | CCl |
| 1.157 | OMe | H | Me | H | Cl | CH |
| 1.158 | OMe | OH | H | Me | Cl | CH |
| 1.159 | OMe | Me | H | H | Cl | CH |
| 1.160 | OMe | OMe | H | H | Cl | CH |
| 1.161 | OMe | H | H | H | CN | N |
| 1.162 | OMe | H | H | H | CN | CH |
| 1.163 | OMe | H | H | H | CN | CMe |
| 1.164 | OMe | H | H | H | CN | CCl |
| 1.165 | OMe | H | Me | H | CN | CH |
| 1.166 | OMe | OH | H | Me | CN | CH |
| 1.167 | OMe | Me | H | H | CN | CH |
| 1.168 | OMe | OMe | H | H | CN | CH |
| 1.169 | OMe | H | H | H | OCF₂H | N |
| 1.170 | OMe | H | H | H | OCF₂H | CH |
| 1.171 | OMe | H | H | H | OCF₂H | CMe |
| 1.172 | OMe | H | H | H | OCF₂H | CCl |
| 1.173 | OMe | H | Me | H | OCF₂H | CH |
| 1.174 | OMe | OH | H | Me | OCF₂H | CH |
| 1.175 | OMe | Me | H | H | OCF₂H | CH |
| 1.176 | OMe | OMe | H | H | OCF₂H | CH |
| 1.177 | OMe | H | H | H | CN | N |
| 1.178 | OMe | H | H | H | CN | CH |
| 1.179 | OMe | H | H | H | CN | CMe |
| 1.180 | OMe | H | H | H | CN | CCl |
| 1.181 | OMe | H | Me | H | CN | CH |
| 1.182 | OMe | OH | H | Me | CN | CH |
| 1.183 | OMe | Me | H | H | CN | CH |

TABLE 1-continued

Compounds of the formula (I) according to the invention in which the substituents and symbols are defined as follows:
Y = Y1    R⁶ = H

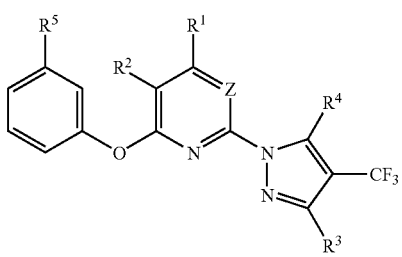

| No. | R¹ | R² | R³ | R⁴ | R⁵ | Z | Physical Data |
|---|---|---|---|---|---|---|---|
| 1.184 | OMe | OMe | H | H | CN | CH | |
| 1.185 | OMe | H | H | H | CN | N | |
| 1.186 | OMe | H | H | H | CN | CH | |
| 1.187 | OMe | H | H | H | CN | CMe | |
| 1.188 | OMe | H | H | H | CN | CCl | |
| 1.189 | OMe | H | Me | H | CN | CH | |
| 1.190 | OMe | CH | H | Me | CN | CH | |
| 1.191 | OMe | Me | H | H | CN | CH | |
| 1.192 | OMe | OMe | H | H | CN | CH | |
| 1.193 | H | OMe | H | H | CF₃ | N | m.p. 100–102° C. |
| 1.194 | H | Cl | H | H | CF₃ | N | m.p. 91–93° C. |
| 1.195 | H | Me | Me | H | CF₃ | N | m.p. 97–99° C. |

Et = ethyl
OMe = methoxy
R$_f$ = retention value
RT = room temperature
OEt = ethoxy
EE = ethyl acetate
i-Pr = isopropyl
Me = methyl
m.p. = melting point
n-Pr = n-propyl

TABLE 2

Compounds of the formula (I) according to the invention in which the substituents and symbols are defined as follows:
Y = Y2    R⁶ = H

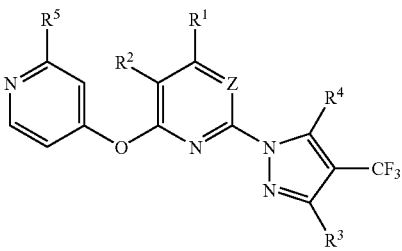

| No. | R¹ | R² | R³ | R⁴ | R⁵ | Z | Physical Data |
|---|---|---|---|---|---|---|---|
| 2.1 | H | H | H | H | CF₃ | N | |
| 2.2 | H | H | H | H | CF₃ | CH | m.p. 73–74° C. |
| 2.3 | H | H | H | H | CF₃ | CMe | |
| 2.4 | H | H | H | H | CF₃ | CCl | |
| 2.5 | H | H | Me | H | CF₃ | CH | m.p. 73–75° C. |
| 2.6 | H | OH | H | Me | CF₃ | CH | |
| 2.7 | H | Me | H | H | CF₃ | N | ¹NMR: δ [CDCl₃] 2.40(s, 3H), 7.50 (dd, 1H), 7.70(d, 1H), 7.95(s, 1H), 8.50(s, 1H), 8.60(s, 1H), 8.85(d, 1H). |
| 2.8 | H | OMe | H | H | CF₃ | CH | |
| 2.9 | H | H | H | H | Cl | N | |
| 2.10 | H | H | H | H | Cl | CH | |
| 2.11 | H | H | H | H | Cl | CMe | |
| 2.12 | H | H | H | H | Cl | CCl | |
| 2.13 | H | H | Me | H | Cl | OH | |
| 2.14 | H | OH | H | Me | Cl | OH | |

TABLE 2-continued

Compounds of the formula (I) according to the invention in which the substituents and symbols are defined as follows:
Y = Y2    R⁶ = H

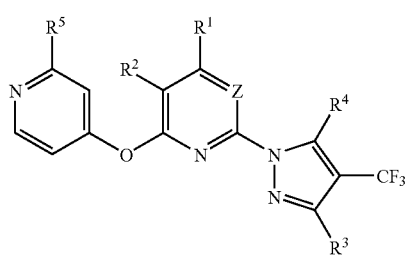

| No. | R¹ | R² | R³ | R⁴ | R⁵ | Z | Physical Data |
|---|---|---|---|---|---|---|---|
| 2.15 | H | Me | H | H | Cl | CH | |
| 2.16 | H | OMe | H | H | Cl | CH | |
| 2.17 | H | H | H | H | CN | N | |
| 2.18 | H | H | H | H | CN | CH | |
| 2.19 | H | H | H | H | CN | CMe | |
| 2.20 | H | H | H | H | CN | CCl | |
| 2.21 | H | H | Me | H | CN | CH | |
| 2.22 | H | OH | H | Me | CN | CH | |
| 2.23 | H | Me | H | H | CN | CH | |
| 2.24 | H | OMe | H | H | CN | CH | |
| 2.25 | H | H | H | H | OCF₂H | N | |
| 2.26 | H | H | H | H | OCF₂H | CH | |
| 2.27 | H | H | H | H | OCF₂H | CMe | |
| 2.28 | H | H | H | H | OCF₂H | CCl | |
| 2.29 | H | H | Me | H | OCF₂H | OH | |
| 2.30 | H | OH | H | Me | OCF₂H | OH | |
| 2.31 | H | Me | H | H | OCF₂H | OH | |
| 2.32 | H | OMe | H | H | OCF₂H | OH | |
| 2.33 | H | H | H | H | CN | N | |
| 2.34 | H | H | H | H | CN | CH | |
| 2.35 | H | H | H | H | CN | CMe | |
| 2.36 | H | H | H | H | CN | CCl | |
| 2.37 | H | H | Me | H | CN | OH | |
| 2.38 | H | OH | H | Me | CN | CH | |
| 2.39 | H | Me | H | H | CN | CH | |
| 2.40 | H | OMe | H | H | CN | CH | |
| 2.41 | H | H | H | H | CN | N | |
| 2.42 | H | H | H | H | CN | CH | |
| 2.43 | H | H | H | H | CN | CMe | |
| 2.44 | H | H | H | H | CN | CCl | |
| 2.45 | H | H | Me | H | CN | OH | |
| 2.46 | H | OH | H | Me | CN | OH | |
| 2.47 | H | Me | H | H | CN | OH | |
| 2.48 | H | OMe | H | H | CN | OH | |
| 2.49 | Me | H | H | H | CF₃ | N | |
| 2.50 | Me | H | H | H | CF₃ | CH | |
| 2.51 | Me | H | H | H | CF₃ | CMe | |
| 2.52 | Me | H | H | H | CF₃ | CCl | |
| 2.53 | Me | H | Me | H | CF₃ | CH | |
| 2.54 | Me | OH | H | Me | CF₃ | CH | |
| 2.55 | Me | Me | H | H | CF₃ | OH | |
| 2.56 | Me | OMe | H | H | CF₃ | OH | |
| 2.57 | Me | H | H | H | Cl | N | |
| 2.58 | Me | H | H | H | Cl | CH | |
| 2.59 | Me | H | H | H | Cl | CMe | |
| 2.60 | Me | H | H | H | Cl | CCl | |
| 2.61 | Me | H | Me | H | Cl | CH | |
| 2.62 | Me | OH | H | Me | Cl | CH | |
| 2.63 | Me | Me | H | H | Cl | CH | |
| 2.64 | Me | OMe | H | H | Cl | CH | |
| 2.65 | Me | H | H | H | CN | N | |
| 2.66 | Me | H | H | H | CN | CH | |
| 2.67 | Me | H | H | H | CN | CMe | |
| 2.68 | Me | H | H | H | CN | CCl | |
| 2.69 | Me | H | Me | H | CN | OH | |
| 2.70 | Me | OH | H | Me | CN | OH | |
| 2.71 | Me | Me | H | H | CN | OH | |
| 2.72 | Me | OMe | H | H | CN | OH | |
| 2.73 | Me | H | H | H | OCF₂H | N | |
| 2.74 | Me | H | H | H | OCF₂H | CH | |

TABLE 2-continued

Compounds of the formula (I) according to the invention in which the substituents and symbols are defined as follows:
Y = Y2   R⁶ = H

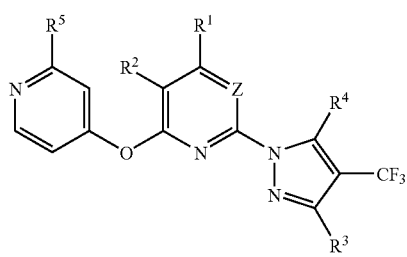

| No. | R¹ | R² | R³ | R⁴ | R⁵ | Z | Physical Data |
|---|---|---|---|---|---|---|---|
| 2.75 | Me | H | H | H | OCF$_2$H | CMe | |
| 2.76 | Me | H | H | H | OCF$_2$H | CCl | |
| 2.77 | Me | H | Me | H | OCF$_2$H | CH | |
| 2.78 | Me | OH | H | Me | OCF$_2$H | CH | |
| 2.79 | Me | Me | H | H | OCF$_2$H | CH | |
| 2.80 | Me | OMe | H | H | OCF$_2$H | CH | |
| 2.81 | Me | H | H | H | CN | N | |
| 2.82 | Me | H | H | H | CN | CH | |
| 2.83 | Me | H | H | H | CN | CMe | |
| 2.84 | Me | H | H | H | CN | CCl | |
| 2.85 | Me | H | Me | H | CN | CH | |
| 2.86 | Me | OH | H | Me | CN | CH | |
| 2.87 | Me | Me | H | H | CN | CH | |
| 2.88 | Me | OMe | H | H | CN | CH | |
| 2.89 | Me | H | H | H | CN | N | |
| 2.90 | Me | H | H | H | CN | CH | |
| 2.91 | Me | H | H | H | CN | OMe | |
| 2.92 | Me | H | H | H | CN | CCl | |
| 2.93 | Me | H | Me | H | CN | CH | |
| 2.94 | Me | OH | H | Me | CN | CH | |
| 2.95 | Me | Me | H | H | CN | CH | |
| 2.96 | Me | OMe | H | H | CN | CH | |
| 2.97 | CN | H | H | H | CF$_3$ | N | m.p. 115–116° C. |
| 2.98 | CN | H | H | H | CF$_3$ | CH | |
| 2.99 | CN | H | H | H | CF$_3$ | OMe | |
| 2.100 | CN | H | H | H | CF$_3$ | CCl | |
| 2.101 | CN | H | Me | H | CF$_3$ | CH | |
| 2.102 | CN | OH | H | Me | CF$_3$ | CH | |
| 2.103 | CN | Me | H | H | CF$_3$ | CH | |
| 2.104 | CN | OMe | H | H | CF$_3$ | CH | |
| 2.105 | CN | H | H | H | Cl | N | |
| 2.106 | CN | H | H | H | Cl | CH | |
| 2.107 | CN | H | H | H | Cl | CMe | |
| 2.108 | CN | H | H | H | Cl | CCl | |
| 2.109 | CN | H | Me | H | Cl | CH | |
| 2.110 | CN | CH | H | Me | Cl | CH | |
| 2.111 | CN | Me | H | H | Cl | CH | |
| 2.112 | CN | OMe | H | H | Cl | CH | |
| 2.113 | CN | H | H | H | CN | N | |
| 2.114 | CN | H | H | H | CN | CH | |
| 2.115 | CN | H | H | H | CN | CMe | |
| 2.116 | CN | H | H | H | CN | CCl | |
| 2.117 | CN | H | Me | H | CN | CH | |
| 2.118 | CN | CH | H | Me | CN | CH | |
| 2.119 | CN | Me | H | H | CN | CH | |
| 2.120 | CN | OMe | H | H | CN | CH | |
| 2.121 | CN | H | H | H | OCF$_2$H | N | |
| 2.122 | CN | H | H | H | OCF$_2$H | CH | |
| 2.123 | CN | H | H | H | OCF$_2$H | OMe | |
| 2.124 | CN | H | H | H | OCF$_2$H | CCl | |
| 2.125 | CN | H | Me | H | OCF$_2$H | CH | |
| 2.126 | CN | CH | H | Me | OCF$_2$H | CH | |
| 2.127 | CN | Me | H | H | OCF$_2$H | CH | |
| 2.128 | CN | OMe | H | H | OCF$_2$H | CH | |
| 2.129 | CN | H | H | H | CN | N | |
| 2.130 | CN | H | H | H | CN | CH | |
| 2.131 | CN | H | H | H | CN | CMe | |
| 2.132 | CN | H | H | H | CN | CCl | |
| 2.133 | CN | H | Me | H | CN | CH | |
| 2.134 | CN | CH | H | Me | CN | CH | |

TABLE 2-continued

Compounds of the formula (I) according to the invention in which the substituents and symbols are defined as follows:
Y = Y2   R⁶ = H

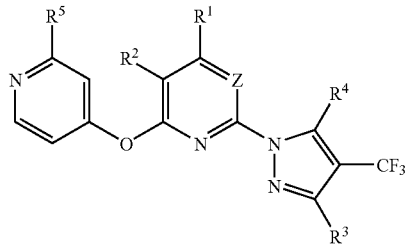

| No. | R¹ | R² | R³ | R⁴ | R⁵ | Z | Physical Data |
|---|---|---|---|---|---|---|---|
| 2.135 | CN | Me | H | H | CN | CH | |
| 2.136 | CN | OMe | H | H | CN | CH | |
| 2.137 | CN | H | H | H | CN | N | |
| 2.138 | CN | H | H | H | CN | CH | |
| 2.139 | CN | H | H | H | CN | CMe | |
| 2.140 | CN | H | H | H | CN | CCl | |
| 2.141 | CN | H | Me | H | CN | CH | |
| 2.142 | CN | CH | H | Me | CN | CH | |
| 2.143 | CN | Me | H | H | CN | CH | |
| 2.144 | CN | OMe | H | H | CN | CH | |
| 2.145 | OMe | H | H | H | CF₃ | N | |
| 2.146 | OMe | H | H | H | CF₃ | CH | |
| 2.147 | OMe | H | H | H | CF₃ | OMe | |
| 2.148 | OMe | H | H | H | CF₃ | CCl | |
| 2.149 | OMe | H | Me | H | CF₃ | CH | |
| 2.150 | OMe | OH | H | Me | CF₃ | CH | |
| 2.151 | OMe | Me | H | H | CF₃ | CH | |
| 2.152 | OMe | OMe | H | H | CF₃ | CH | |
| 2.153 | OMe | H | H | H | Cl | N | |
| 2.154 | OMe | H | H | H | Cl | CH | |
| 2.155 | OMe | H | H | H | Cl | CMe | |
| 2.156 | OMe | H | H | H | Cl | CCl | |
| 2.157 | OMe | H | Me | H | Cl | CH | |
| 2.158 | OMe | CH | H | Me | Cl | CH | |
| 2.159 | OMe | Me | H | H | Cl | CH | |
| 2.160 | OMe | OMe | H | H | Cl | CH | |
| 2.161 | OMe | H | H | H | CN | N | |
| 2.162 | OMe | H | H | H | CN | CH | |
| 2.163 | OMe | H | H | H | CN | CMe | |
| 2.164 | OMe | H | H | H | CN | CCl | |
| 2.165 | OMe | H | Me | H | CN | CH | |
| 2.166 | OMe | OH | H | Me | CN | CH | |
| 2.167 | OMe | Me | H | H | CN | CH | |
| 2.168 | OMe | OMe | H | H | CN | CH | |
| 2.169 | OMe | H | H | H | OCF₂H | N | |
| 2.170 | OMe | H | H | H | OCF₂H | CH | |
| 2.171 | OMe | H | H | H | OCF₂H | OMe | |
| 2.172 | OMe | H | H | H | OCF₂H | CCl | |
| 2.173 | OMe | H | Me | H | OCF₂H | CH | |
| 2.174 | OMe | OH | H | Me | OCF₂H | CH | |
| 2.175 | OMe | Me | H | H | OCF₂H | CH | |
| 2.176 | OMe | OMe | H | H | OCF₂H | CH | |
| 2.177 | OMe | H | H | H | CN | N | |
| 2.178 | OMe | H | H | H | CN | CH | |
| 2.179 | OMe | H | H | H | CN | CMe | |
| 2.180 | OMe | H | H | H | CN | CCl | |
| 2.181 | OMe | H | Me | H | CN | CH | |
| 2.182 | OMe | OH | H | Me | CN | CH | |
| 2.183 | OMe | Me | H | H | CN | CH | |
| 2.184 | OMe | OMe | H | H | CN | CH | |
| 2.185 | OMe | H | H | H | CN | N | |
| 2.186 | OMe | H | H | H | CN | CH | |
| 2.187 | OMe | H | H | H | CN | CMe | |
| 2.188 | OMe | H | H | H | CN | CCl | |
| 2.189 | OMe | H | Me | H | CN | CH | |
| 2.190 | OMe | OH | H | Me | CN | CH | |
| 2.191 | OMe | Me | H | H | CN | CH | |
| 2.192 | OMe | OMe | H | H | CN | CH | |
| 2.193 | H | OMe | H | H | CF₃ | N | m.p. 137–139° C. |
| 2.194 | H | Br | H | H | CF₃ | N | m.p. 101–103° C. |

TABLE 2-continued

Compounds of the formula (I) according to the invention in which the substituents and symbols are defined as follows:
Y = Y2    R⁶ = H

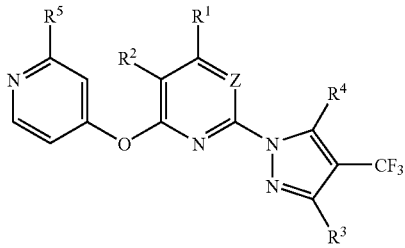

| No. | R¹ | R² | R³ | R⁴ | R⁵ | Z | Physical Data |
|---|---|---|---|---|---|---|---|
| 2.195 | H | Cl | H | H | CF₃ | N | m.p. 119–121° C. |
| 2.196 | H | Me | H | Me | CF₃ | N | ¹N-NMR: 2.10(s, 3H); 2.40(s, 3H); 6.95(dd, 1H); 7.20(d, 1H); 7.75(s, 1H); 8.35(d, 1H); 8.60(s, 1H) |

TABLE 3

Compounds of the formula (I) according to the invention in which the substituents and symbols are defined as follows:
Y = Y3    R⁶ = H

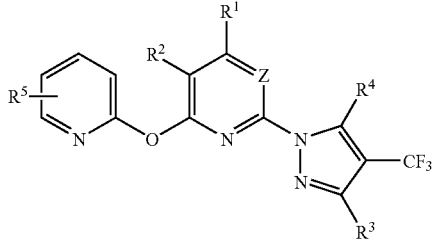
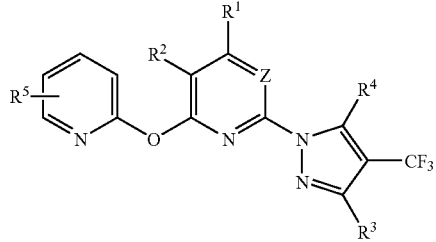

| No. | R¹ | R² | R³ | R⁴ | R⁵ | Z | Physical Data |
|---|---|---|---|---|---|---|---|
| 3.1 | H | H | H | H | CF₃ | N | |
| 3.2 | H | H | H | H | CF₃ | CH | |
| 3.3 | H | H | H | H | CF₃ | CMe | |
| 3.4 | H | H | H | H | CF₃ | CCl | |
| 3.5 | H | H | Me | H | CF₃ | CH | |
| 3.6 | H | OH | H | Me | CF₃ | CH | |
| 3.7 | H | Me | H | H | CF₃ | CH | |
| 3.8 | H | OMe | H | H | CF₃ | CH | |
| 3.9 | H | H | H | H | Cl | N | |
| 3.10 | H | H | H | H | Cl | CH | |
| 3.11 | H | H | H | H | Cl | CMe | |
| 3.12 | H | H | H | H | Cl | CCl | |
| 3.13 | H | H | Me | H | Cl | CH | |
| 3.14 | H | OH | H | Me | Cl | CH | |
| 3.15 | H | Me | H | H | Cl | CH | |
| 3.16 | H | OMe | H | H | Cl | CH | |
| 3.17 | H | H | H | H | CN | N | |
| 3.18 | H | H | H | H | CN | CH | |
| 3.19 | H | H | H | H | CN | CMe | |
| 3.20 | H | H | H | H | CN | CCl | |
| 3.21 | H | H | Me | H | CN | CH | |
| 3.22 | H | OH | H | Me | CN | CH | |
| 3.23 | H | Me | H | H | CN | CH | |
| 3.24 | H | OMe | H | H | CN | CH | |
| 3.25 | H | H | H | H | OCF₂H | N | |
| 3.26 | H | H | H | H | OCF₂H | CH | |
| 3.27 | H | H | H | H | OCF₂H | OMe | |
| 3.28 | H | H | H | H | OCF₂H | CCl | |
| 3.29 | H | H | Me | H | OCF₂H | CH | |
| 3.30 | H | OH | H | Me | OCF₂H | CH | |
| 3.31 | H | Me | H | H | OCF₂H | CH | |
| 3.32 | H | OMe | H | H | OCF₂H | CH | |
| 3.33 | H | H | H | H | CN | N | |
| 3.34 | H | H | H | H | CN | CH | |
| 3.35 | H | H | H | H | CN | OMe | |
| 3.36 | H | H | H | H | CN | CCl | |
| 3.37 | H | H | Me | H | CN | CH | |
| 3.38 | H | OH | H | Me | CN | CH | |
| 3.39 | H | Me | H | H | CN | CH | |
| 3.40 | H | OMe | H | H | CN | CH | |
| 3.41 | H | H | H | H | CN | N | |
| 3.42 | H | H | H | H | CN | CH | |
| 3.43 | H | H | H | H | CN | OMe | |
| 3.44 | H | H | H | H | CN | CCl | |
| 3.45 | H | H | Me | H | CN | CH | |
| 3.46 | H | OH | H | Me | CN | CH | |
| 3.47 | H | Me | H | H | CN | CH | |
| 3.48 | H | OMe | H | H | CN | CH | |
| 3.49 | Me | H | H | H | CF₃ | N | |
| 3.50 | Me | H | H | H | CF₃ | CH | |
| 3.51 | Me | H | H | H | CF₃ | CMe | |
| 3.52 | Me | H | H | H | CF₃ | CCl | |
| 3.53 | Me | H | Me | H | CF₃ | CH | |
| 3.54 | Me | OH | H | Me | CF₃ | CH | |
| 3.55 | Me | Me | H | H | CF₃ | CH | |
| 3.56 | Me | OMe | H | H | CF₃ | CH | |
| 3.57 | Me | H | H | H | Cl | N | |
| 3.58 | Me | H | H | H | Cl | CH | |
| 3.59 | Me | H | H | H | Cl | CMe | |
| 3.60 | Me | H | H | H | Cl | CCl | |
| 3.61 | Me | H | Me | H | Cl | CH | |
| 3.62 | Me | OH | H | Me | Cl | CH | |

TABLE 3-continued

Compounds of the formula (I) according to the invention in which the substituents and symbols are defined as follows:
Y = Y3   $R^6$ = H

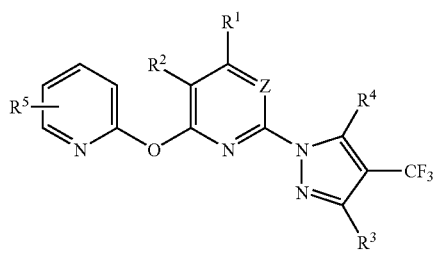

| No. | $R^1$ | $R^2$ | $R^3$ | $R^4$ | $R^5$ | Z | Physical Data |
|---|---|---|---|---|---|---|---|
| 3.63 | Me | Me | H | H | Cl | CH | |
| 3.64 | Me | OMe | H | H | Cl | CH | |
| 3.65 | Me | H | H | H | CN | N | |
| 3.66 | Me | H | H | H | CN | CH | |
| 3.67 | Me | H | H | H | CN | CMe | |
| 3.68 | Me | H | H | H | CN | CCl | |
| 3.69 | Me | H | Me | H | CN | CH | |
| 3.70 | Me | OH | H | Me | CN | CH | |
| 3.71 | Me | Me | H | H | CN | CH | |
| 3.72 | Me | OMe | H | H | CN | CH | |
| 3.73 | Me | H | H | H | $OCF_2H$ | N | |
| 3.74 | Me | H | H | H | $OCF_2H$ | CH | |
| 3.75 | Me | H | H | H | $OCF_2H$ | CMe | |
| 3.76 | Me | H | H | H | $OCF_2H$ | CCl | |
| 3.77 | Me | H | Me | H | $OCF_2H$ | CH | |
| 3.78 | Me | OH | H | Me | $OCF_2H$ | CH | |
| 3.79 | Me | Me | H | H | $OCF_2H$ | CH | |
| 3.80 | Me | OMe | H | H | $OCF_2H$ | CH | |
| 3.81 | Me | H | H | H | CN | N | |
| 3.82 | Me | H | H | H | CN | CH | |
| 3.83 | Me | H | H | H | CN | OMe | |
| 3.84 | Me | H | H | H | CN | CCl | |
| 3.85 | Me | H | Me | H | CN | CH | |
| 3.86 | Me | OH | H | Me | CN | CH | |
| 3.87 | Me | Me | H | H | CN | CH | |
| 3.88 | Me | OMe | H | H | CN | CH | |
| 3.89 | Me | H | H | H | CN | N | |
| 3.90 | Me | H | H | H | CN | CH | |
| 3.91 | Me | H | H | H | CN | CMe | |
| 3.92 | Me | H | H | H | CN | CCl | |
| 3.93 | Me | H | Me | H | CN | CH | |
| 3.94 | Me | OH | H | Me | CN | CH | |
| 3.95 | Me | Me | H | H | CN | CH | |
| 3.96 | Me | OMe | H | H | CN | CH | |
| 3.97 | CN | H | H | H | $CF_3$ | N | |
| 3.98 | CN | H | H | H | $CF_3$ | CH | |
| 3.99 | CN | H | H | H | $CF_3$ | CMe | |
| 3.100 | CN | H | H | H | $CF_3$ | CCl | |
| 3.101 | CN | H | Me | H | $CF_3$ | CH | |
| 3.102 | CN | OH | H | Me | $CF_3$ | CH | |
| 3.103 | CN | Me | H | H | $CF_3$ | CH | |
| 3.104 | CN | OMe | H | H | $CF_3$ | CH | |
| 3.105 | CN | H | H | H | Cl | N | |
| 3.106 | CN | H | H | H | Cl | CH | |
| 3.107 | CN | H | H | H | Cl | CMe | |
| 3.108 | CN | H | H | H | Cl | CCl | |
| 3.109 | CN | H | Me | H | Cl | CH | |
| 3.110 | CN | OH | H | Me | Cl | CH | |
| 3.111 | CN | Me | H | H | Cl | CH | |
| 3.112 | CN | OMe | H | H | Cl | CH | |
| 3.113 | CN | H | H | H | CN | N | |
| 3.114 | CN | H | H | H | CN | CH | |
| 3.115 | CN | H | H | H | CN | OMe | |
| 3.116 | CN | H | H | H | CN | CCl | |
| 3.117 | CN | H | Me | H | CN | CH | |
| 3.118 | CN | OH | H | Me | CN | CH | |
| 3.119 | CN | Me | H | H | CN | CH | |
| 3.120 | CN | OMe | H | H | CN | CH | |
| 3.121 | CN | H | H | H | $OCF_2H$ | N | |
| 3.122 | CN | H | H | H | $OCF_2H$ | CH | |
| 3.123 | CN | H | H | H | $OCF_2H$ | CMe | |
| 3.124 | CN | H | H | H | $OCF_2H$ | CCl | |
| 3.125 | CN | H | Me | H | $OCF_2H$ | CH | |
| 3.126 | CN | OH | H | Me | $OCF_2H$ | CH | |
| 3.127 | CN | Me | H | H | $OCF_2H$ | CH | |
| 3.128 | CN | OMe | H | H | $OCF_2H$ | CH | |
| 3.129 | CN | H | H | H | CN | N | |
| 3.130 | CN | H | H | H | CN | CH | |
| 3.131 | CN | H | H | H | CN | CMe | |
| 3.132 | CN | H | H | H | CN | CCl | |
| 3.133 | CN | H | Me | H | CN | CH | |
| 3.134 | CN | OH | H | Me | CN | CH | |
| 3.135 | CN | Me | H | H | CN | CH | |
| 3.136 | CN | OMe | H | H | CN | CH | |
| 3.137 | CN | H | H | H | CN | N | |
| 3.138 | CN | H | H | H | CN | CH | |
| 3.139 | CN | H | H | H | CN | CMe | |
| 3.140 | CN | H | H | H | CN | CCl | |
| 3.141 | CN | H | Me | H | CN | CH | |
| 3.142 | CN | OH | H | Me | CN | CH | |
| 3.143 | CN | Me | H | H | CN | CH | |
| 3.144 | CN | OMe | H | H | CN | CH | |
| 3.145 | OMe | H | H | H | $CF_3$ | N | |
| 3.146 | OMe | H | H | $CF_3$ | CH | | |
| 3.147 | OMe | H | H | H | $CF_3$ | CMe | |
| 3.148 | OMe | H | H | H | $CF_3$ | CCl | |
| 3.149 | OMe | H | Me | H | $CF_3$ | CH | |
| 3.150 | OMe | OH | H | Me | $CF_3$ | CH | |
| 3.151 | OMe | Me | H | H | $CF_3$ | CH | |
| 3.152 | OMe | OMe | H | H | $CF_3$ | CH | |
| 3.153 | OMe | H | H | H | Cl | N | |
| 3.154 | OMe | H | H | H | Cl | CH | |
| 3.155 | OMe | H | H | H | Cl | CMe | |
| 3.156 | OMe | H | H | H | Cl | CCl | |
| 3.157 | OMe | H | Me | H[] | Cl | CH | |
| 3.158 | OMe | OH | H | Me | Cl | CH | |
| 3.159 | OMe | Me | H | H | Cl | CH | |
| 3.160 | OMe | OMe | H | H | Cl | CH | |
| 3.161 | OMe | H | H | H | CN | N | |
| 3.162 | OMe | H | H | H | CN | CH | |
| 3.163 | OMe | H | H | H | CN | CMe | |
| 3.164 | OMe | H | H | H | CN | CCl | |
| 3.165 | OMe | H | Me | H | CN | CH | |
| 3.166 | OMe | OH | H | Me | CN | CH | |
| 3.167 | OMe | Me | H | H | CN | CH | |
| 3.168 | OMe | OMe | H | H | CN | CH | |
| 3.169 | OMe | H | H | H | $OCF_2H$ | N | |
| 3.170 | OMe | H | H | H | $OCF_2H$ | CH | |
| 3.171 | OMe | H | H | H | $OCF_2H$ | CMe | |
| 3.172 | OMe | H | H | H | $OCF_2H$ | CCl | |
| 3.173 | OMe | H | Me | H | $OCF_2H$ | CH | |
| 3.174 | OMe | OH | H | Me | $OCF_2H$ | CH | |
| 3.175 | OMe | Me | H | H | $OCF_2H$ | CH | |
| 3.176 | OMe | OMe | H | H | $OCF_2H$ | CH | |
| 3.177 | OMe | H | H | H | CN | N | |
| 3.178 | OMe | H | H | H | CN | CH | |
| 3.179 | OMe | H | H | H | CN | CMe | |
| 3.180 | OMe | H | H | H | CN | CCl | |
| 3.181 | OMe | H | Me | H | CN | CH | |

TABLE 3-continued

Compounds of the formula (I) according to the invention in which the substituents and symbols are defined as follows:
Y = Y3   R⁶ = H

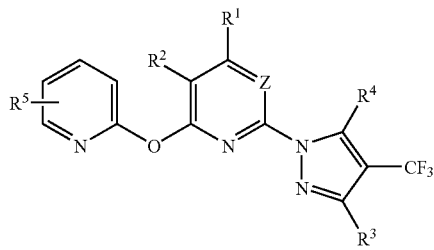

| No. | R¹ | R² | R³ | R⁴ | R⁵ | Z | Physical Data |
|---|---|---|---|---|---|---|---|
| 3.182 | OMe | OH | H | Me | CN | CH | |
| 3.183 | OMe | Me | H | H | CN | CH | |
| 3.184 | OMe | OMe | H | H | CN | CH | |
| 3.185 | OMe | H | H | H | CN | N | |
| 3.186 | OMe | H | H | H | CN | CH | |
| 3.187 | OMe | H | H | H | CN | CMe | |
| 3.188 | OMe | H | H | H | CN | CCl | |
| 3.189 | OMe | H | Me | H | CN | CH | |
| 3.190 | OMe | OH | H | Me | CN | CH | |
| 3.191 | OMe | Me | H | H | CN | CH | |
| 3.192 | OMe | OMe | H | H | CN | CH | |

TABLE 4

Compounds of the formula (I) according to the invention in which the substituents and symbols are defined as follows:
Y = Y4   R⁶ = H   R⁷ = Me

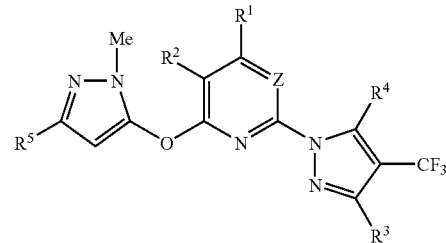

| No. | R¹ | R² | R³ | R⁴ | R⁵ | Z | Physical Data |
|---|---|---|---|---|---|---|---|
| 4.1 | H | H | H | H | CF₃ | N | ¹H NMR: δ [CDCl₃] 3.82(s, 3H), 6.60(s, 1H), 7.05(d, 1H), 8.00(s, 1H), 8.65(s, 1H), 8.80(d, 1H) |
| 4.2 | H | H | H | H | CF₃ | N | ¹H NMR (CDCl₃/TMS): δ (ppm) = 8.43 (s, 1H), 7.97(t, 1H), 7.88(s, 1H), 7.82(d, 1H), 7.00(d, 1H), 6.34(s, 1H), 3.82(s, 3H). |
| 4.3 | H | H | H | H | CF₃ | CMe | |
| 4.4 | H | H | H | H | CF₃ | CCl | |
| 4.5 | H | H | Me | H | CF₃ | CH | m.p. 95–96° C. |
| 4.6 | H | OH | H | Me | CF₃ | CH | |
| 4.7 | H | Me | H | H | CF₃ | CH | |
| 4.8 | H | OMe | H | H | CF₃ | CH | |
| 4.9 | H | H | H | H | Cl | N | |
| 4.10 | H | H | H | H | Cl | CH | |
| 4.11 | H | H | H | H | Cl | CMe | |
| 4.12 | H | H | H | H | Cl | CCl | |
| 4.13 | H | H | Me | H | Cl | CH | |
| 4.14 | H | OH | H | Me | Cl | CH | |
| 4.15 | H | Me | H | H | Cl | CH | |
| 4.16 | H | OMe | H | H | Cl | CH | |
| 4.17 | H | H | H | H | CN | N | |
| 4.18 | H | H | H | H | CN | CH | |
| 4.19 | H | H | H | H | CN | CMe | |
| 4.20 | H | H | H | H | CN | CCl | |
| 4.21 | H | H | Me | H | CN | CH | |
| 4.22 | H | OH | H | Me | CN | CH | |
| 4.23 | H | Me | H | H | CN | CH | |

TABLE 4-continued

Compounds of the formula (I) according to the invention in which the substituents and symbols are defined as follows:
Y = Y4   R⁶ = H   R⁷ = Me

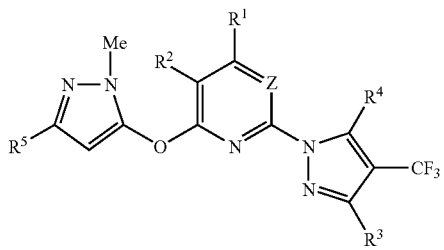

| No. | R¹ | R² | R³ | R⁴ | R⁵ | Z | Physical Data |
|---|---|---|---|---|---|---|---|
| 4.24 | H | OMe | H | H | CN | CH | |
| 4.25 | H | H | H | H | OCF₂H | N | |
| 4.26 | H | H | H | H | OCF₂H | CH | |
| 4.27 | H | H | H | H | OCF₂H | CMe | |
| 4.28 | H | H | H | H | OCF2H | CCl | |
| 4.29 | H | H | Me | H | OCF₂H | CH | |
| 4.30 | H | OH | H | Me | OCF₂H | CH | |
| 4.31 | H | Me | H | H | OCF2H | CH | |
| 4.32 | H | OMe | H | H | OCF2H | CH | |
| 4.33 | H | H | H | H | CN | N | |
| 4.34 | H | H | H | H | CN | CH | |
| 4.35 | H | H | H | H | CN | OMe | |
| 4.36 | H | H | H | H | CN | 001 | |
| 4.37 | H | H | Me | H | CN | 0H | |
| 4.38 | H | OH | H | Me | CN | CH | |
| 4.39 | H | Me | H | H | CN | CH | |
| 4.40 | H | OMe | H | H | CN | CH | |
| 4.41 | H | H | H | H | CN | N | |
| 4.42 | H | H | H | H | CN | CH | |
| 4.43 | H | H | H | H | CN | OMe | |
| 4.44 | H | H | H | H | CN | CCl | |
| 4.45 | H | H | Me | H | CN | CH | |
| 4.46 | H | OH | H | Me | CN | CH | |
| 4.47 | H | Me | H | H | CN | CH | |
| 4.48 | H | OMe | H | H | CN | CH | |
| 4.49 | Me | H | H | H | CF₃ | N | m.p. 122–124° C. |
| 4.50 | Me | H | H | H | CF₃ | CH | ¹H NMR (CDCl₃/TMS): δ (ppm) 8.43 (s, 1H), 7.86(s, 1H), 7.67(s, 1H), 6.82 (s, 1H), 6.30(s, 1H), 3.82(s, 3H), 2.50 (s, 3H). |
| 4.51 | Me | H | H | H | CF₃ | CMe | |
| 4.52 | Me | H | H | H | CF₃ | CCl | |
| 4.53 | Me | H | Me | H | CF₃ | CH | |
| 4.54 | Me | OH | H | Me | CF₃ | CH | |
| 4.55 | Me | Me | H | H | CF₃ | CH | |
| 4.56 | Me | OMe | H | H | CF₃ | CH | |
| 4.57 | Me | H | H | H | Cl | N | |
| 4.58 | Me | H | H | H | Cl | CH | |
| 4.59 | Me | H | H | H | Cl | CMe | |
| 4.60 | Me | H | H | H | Cl | CCl | |
| 4.61 | Me | H | Me | H | Cl | CH | |
| 4.62 | Me | OH | H | Me | Cl | CH | |
| 4.63 | Me | Me | H | H | Cl | CH | |
| 4.64 | Me | OMe | H | H | Cl | CH | |
| 4.65 | Me | H | H | H | CN | N | |
| 4.66 | Me | H | H | H | CN | CH | |
| 4.67 | Me | H | H | H | CN | CMe | |
| 4.68 | Me | H | H | H | CN | CCl | |
| 4.69 | Me | H | Me | H | CN | CH | |
| 4.70 | Me | CH | H | Me | CN | CH | |
| 4.71 | Me | Me | H | H | CN | CH | |
| 4.72 | Me | OMe | H | H | CN | CH | |
| 4.73 | Me | H | H | H | OCF₂H | N | |
| 4.74 | Me | H | H | H | OCF₂H | CH | |
| 4.75 | Me | H | H | H | OCF₂H | CMe | |
| 4.76 | Me | H | H | H | OCF₂H | CCl | |
| 4.77 | Me | H | Me | H | OCF₂H | CH | |
| 4.78 | Me | OH | H | Me | OCF₂H | CH | |
| 4.79 | Me | Me | H | H | OCF₂H | CH | |
| 4.80 | Me | OMe | H | H | OCF₂H | CH | |

TABLE 4-continued

Compounds of the formula (I) according to the invention in which the substituents and symbols are defined as follows:
Y = Y4    R⁶ = H    R⁷ = Me

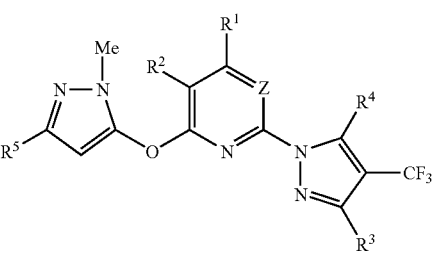

| No. | R¹ | R² | R³ | R⁴ | R⁵ | Z | Physical Data |
|---|---|---|---|---|---|---|---|
| 4.81 | Me | H | H | H | CN | N | |
| 4.82 | Me | H | H | H | CN | CH | |
| 4.83 | Me | H | H | H | CN | CMe | |
| 4.84 | Me | H | H | H | CN | CCl | |
| 4.85 | Me | H | Me | H | CN | CH | |
| 4.86 | Me | OH | H | Me | CN | CH | |
| 4.87 | Me | Me | H | H | CN | CH | |
| 4.88 | Me | OMe | H | H | CN | CH | |
| 4.89 | Me | H | H | H | CN | N | |
| 4.90 | Me | H | H | H | CN | CH | |
| 4.91 | Me | H | H | H | CN | CMe | |
| 4.92 | Me | H | H | H | CN | CCl | |
| 4.93 | Me | H | Me | H | CN | CH | |
| 4.94 | Me | OH | H | Me | CN | CH | |
| 4.95 | Me | Me | H | H | CN | CH | |
| 4.96 | Me | CMe | H | H | CN | CH | |
| 4.97 | CN | H | H | H | CF₃ | N | |
| 4.98 | CN | H | H | H | CF₃ | CH | R_f = 0.63; heptane/ethyl acetate 1:1 |
| 4.99 | CN | H | H | H | CF₃ | CMe | |
| 4.100 | CN | H | H | H | CF₃ | CCl | |
| 4.101 | CN | H | Me | H | CF₃ | CH | ¹H NMR [CDCl₃]: 2.42(s, 3H); 3,86(s, 3H); 6.36(s, 1H); 7.19(s, 1H); 8.02(s, 1H); 8.30(s, 1H) |
| 4.102 | CN | OH | H | Me | CF₃ | CH | |
| 4.103 | CN | Me | H | H | CF₃ | CH | |
| 4.104 | CN | OMe | H | H | CF₃ | CH | |
| 4.105 | CN | H | H | H | Cl | N | |
| 4.106 | CN | H | H | H | Cl | CH | |
| 4.107 | CN | H | H | H | Cl | OMe | |
| 4.108 | CN | H | H | H | Cl | CCl | |
| 4.109 | CN | H | Me | H | Cl | CH | |
| 4.110 | CN | OH | H | Me | Cl | CH | |
| 4.111 | CN | Me | H | H | Cl | CH | |
| 4.112 | CN | OMe | H | H | Cl | CH | |
| 4.113 | CN | H | H | H | CN | N | |
| 4.114 | CN | H | H | H | CN | CH | |
| 4.115 | CN | H | H | H | CN | OMe | |
| 4.116 | CN | H | H | H | CN | CCl | |
| 4.117 | CN | H | Me | H | CN | CH | |
| 4.118 | CN | OH | H | Me | CN | CH | |
| 4.119 | CN | Me | H | H | CN | CH | |
| 4.120 | CN | OMe | H | H | CN | CH | |
| 4.121 | CN | H | H | H | OCF₂H | N | |
| 4.122 | CN | H | H | H | OCF₂H | CH | |
| 4.123 | CN | H | H | H | OCF₂H | CMe | |
| 4.124 | CN | H | H | H | OCF₂H | CCl | |
| 4.125 | CN | H | Me | H | OCF₂H | CH | |
| 4.126 | CN | OH | H | Me | OCF₂H | CH | |
| 4.127 | CN | Me | H | H | OCF₂H | CH | |
| 4.128 | CN | OMe | H | H | OCF₂H | CH | |
| 4.129 | CN | H | H | H | CN | N | |
| 4.130 | CN | H | H | H | CN | CH | |
| 4.131 | CN | H | H | H | CN | CMe | |
| 4.132 | CN | H | H | H | CN | CCl | |
| 4.133 | CN | H | Me | H | CN | CH | |
| 4.134 | CN | OH | H | Me | CN | CH | |
| 4.135 | CN | Me | H | H | CN | CH | |
| 4.136 | CN | OMe | H | H | CN | CH | |
| 4.137 | CN | H | H | H | CN | N | |
| 4.138 | CN | H | H | H | CN | CH | |

TABLE 4-continued

Compounds of the formula (I) according to the invention in which the substituents and symbols are defined as follows:
Y = Y4    R⁶ = H    R⁷ = Me

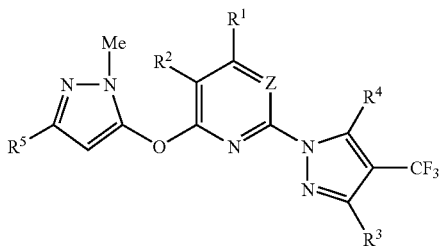

| No. | R¹ | R² | R³ | R⁴ | R⁵ | Z | Physical Data |
|---|---|---|---|---|---|---|---|
| 4.139 | CN | H | H | H | CN | CMe | |
| 4.140 | CN | H | H | H | CN | CCl | |
| 4.141 | CN | H | Me | H | CN | CH | |
| 4.142 | CN | OH | H | Me | CN | CH | |
| 4.143 | CN | Me | H | H | CN | CH | |
| 4.144 | CN | OMe | H | H | CN | CH | |
| 4.145 | OMe | H | H | H | CF₃ | N | |
| 4.146 | OMe | H | H | H | CF₃ | CH | ¹H NMR(CDCl₃/TMS): δ (ppm) 8.42 (s, 1H), 7.85(s, 1H), 7.40(d, 1H), 6.44 (d, 1H,), 6.29(s, 1H), 3.99(s, 3H), 3.81 (s, 3H). |
| 4.147 | OMe | H | H | H | CF₃ | CMe | |
| 4.148 | OMe | H | H | H | CF₃ | CCl | |
| 4.149 | OMe | H | Me | H | CF₃ | CH | |
| 4.150 | OMe | OH | H | Me | CF₃ | CH | |
| 4.151 | OMe | Me | H | H | CF₃ | CH | |
| 4.152 | OMe | OMe | H | H | CF₃ | CH | |
| 4.153 | OMe | H | H | H | Of | N | |
| 4.154 | OMe | H | H | H | Cl | CH | |
| 4.155 | OMe | H | H | H | Cl | OMe | |
| 4.156 | OMe | H | H | H | Cl | CCl | |
| 4.157 | OMe | H | Me | H | Cl | CH | |
| 4.158 | OMe | OH | H | Me | Cl | CH | |
| 4.159 | OMe | Me | H | H | Cl | CH | |
| 4.160 | OMe | OMe | H | H | Cl | CH | |
| 4.161 | OMe | H | H | H | CN | N | |
| 4.162 | OMe | H | H | H | CN | CH | |
| 4.163 | OMe | H | H | H | CN | OMe | |
| 4.164 | OMe | H | H | H | CN | CCl | |
| 4.165 | OMe | H | Me | H | CN | CH | |
| 4.166 | OMe | OH | H | Me | CN | CH | |
| 4.167 | OMe | Me | H | H | CN | CH | |
| 4.168 | OMe | OMe | H | H | CN | CH | |
| 4.169 | OMe | H | H | H | OCF₂H | N | |
| 4.170 | OMe | H | H | H | OCF₂H | CH | |
| 4.171 | OMe | H | H | H | OCF₂H | CMe | |
| 4.172 | OMe | H | H | H | OCF₂H | CCl | |
| 4.173 | OMe | H | Me | H | OCF₂H | CH | |
| 4.174 | OMe | OH | H | Me | OCF₂H | CH | |
| 4.175 | OMe | Me | H | H | OCF₂H | CH | |
| 4.176 | OMe | OMe | H | H | OCF₂H | CH | |
| 4.177 | OMe | H | H | H | CN | N | |
| 4.178 | OMe | H | H | H | CN | CH | |
| 4.179 | OMe | H | H | H | CN | CMe | |
| 4.180 | OMe | H | H | H | CN | CCl | |
| 4.181 | OMe | H | Me | H | CN | CH | |
| 4.182 | OMe | OH | H | Me | CN | CH | |
| 4.183 | OMe | Me | H | H | CN | CH | |
| 4.184 | OMe | OMe | H | H | CN | CH | |
| 4.185 | OMe | H | H | H | CN | N | |
| 4.186 | OMe | H | H | H | CN | CH | |
| 4.187 | OMe | H | H | H | CN | CMe | |
| 4.188 | OMe | H | H | H | CN | CCl | |
| 4.189 | OMe | H | Me | H | CN | CH | |
| 4.190 | OMe | OH | H | Me | CN | CH | |
| 4.191 | OMe | Me | H | H | CN | CH | |
| 4.192 | OMe | OMe | H | H | CN | CH | |
| 4.193 | H | Cl | H | H | CF₃ | N | m.p. 113–115° C. |
| 4.194 | Et | H | H | H | CF₃ | N | m.p. 106–108° C. |
| 4.195 | Et | H | Me | H | CF₃ | N | m.p. 121–123° C. |

TABLE 4-continued

Compounds of the formula (I) according to the invention in which the substituents and symbols are defined as follows:

Y = Y4    R⁶ = H    R⁷ = Me

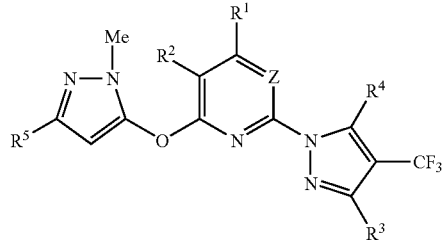

| No. | R¹ | R² | R³ | R⁴ | R⁵ | Z | Physical Data |
|---|---|---|---|---|---|---|---|
| 4.196 | Et | H | H | Me | CF₃ | N | ¹H NMR [CDCl₃]: 1.40(t, 3H); 2.95(q, 2H); 2.50(s, 3H); 3.80(s, 3H); 6.45(s, 1H); 6.90(s, 1H); 7.88(s, 1H) |

TABLE 5

Compounds of the formula (I) according to the invention in which the substituents and symbols are defined as follows:

Y = Y4    R⁶ = H    R⁷ = Me

| No. | R¹ | R² | R³ | R⁴ | R⁵ | Z | Physical Data |
|---|---|---|---|---|---|---|---|
| 5.1 | H | H | H | H | CF₃ | N | |
| 5.2 | H | H | H | H | CF₃ | CH | |
| 5.3 | H | H | H | H | CF₃ | CMe | |
| 5.4 | H | H | H | H | CF₃ | CCl | |
| 5.5 | H | H | Me | H | CF₃ | CH | |
| 5.6 | H | OH | H | Me | CF₃ | CH | |
| 5.7 | H | Me | H | H | CF₃ | CH | |
| 5.8 | H | OMe | H | H | CF₃ | CH | |
| 5.9 | H | H | H | H | Cl | N | |
| 5.10 | H | H | H | H | Cl | CH | |
| 5.11 | H | H | H | H | Cl | CMe | |
| 5.12 | H | H | H | H | Cl | CCl | |
| 5.13 | H | H | Me | H | Cl | CH | |
| 5.14 | H | OH | H | Me | Cl | CH | |
| 5.15 | H | Me | H | H | Cl | CH | |
| 5.16 | H | OMe | H | H | Cl | CH | |
| 5.17 | H | H | H | H | CN | N | |
| 5.18 | H | H | H | H | CN | CH | |
| 5.19 | H | H | H | H | CN | CMe | |
| 5.20 | H | H | H | H | CN | CCl | |
| 5.21 | H | H | Me | H | CN | CH | |
| 5.22 | H | OH | H | Me | CN | CH | |
| 5.23 | H | Me | H | H | CN | CH | |
| 5.24 | H | OMe | H | H | CN | CH | |
| 5.25 | H | H | H | H | OCF₂H | N | |
| 5.26 | H | H | H | H | OCF₂H | CH | |
| 5.27 | H | H | H | H | OCF₂H | CMe | |
| 5.28 | H | H | H | H | OCF₂H | CCl | |
| 5.29 | H | H | Me | H | OCF₂H | CH | |
| 5.30 | H | OH | H | Me | OCF₂H | CH | |
| 5.31 | H | Me | H | H | OCF₂H | CH | |
| 5.32 | H | OMe | H | H | OCF₂H | CH | |
| 5.33 | H | H | H | H | CN | N | |
| 5.34 | H | H | H | H | CN | CH | |
| 5.35 | H | H | H | H | CN | CMe | |
| 5.36 | H | H | H | H | CN | CCl | |
| 5.37 | H | H | Me | H | CN | CH | |
| 5.38 | H | OH | H | Me | CN | CH | |
| 5.39 | H | Me | H | H | CN | CH | |
| 5.40 | H | OMe | H | H | CN | CH | |
| 5.41 | H | H | H | H | CN | N | |
| 5.42 | H | H | H | H | CN | CH | |
| 5.43 | H | H | H | H | CN | CMe | |
| 5.44 | H | H | H | H | CN | CCl | |
| 5.45 | H | H | Me | H | CN | CH | |
| 5.46 | H | OH | H | Me | CN | CH | |
| 5.47 | H | Me | H | H | CN | CH | |
| 5.48 | H | OMe | H | H | CN | CH | |
| 5.49 | Me | H | H | H | CF₃ | N | |
| 5.50 | Me | H | H | H | CF₃ | CH | |
| 5.51 | Me | H | H | H | CF₃ | CMe | |
| 5.52 | Me | H | H | H | CF₃ | CCl | |
| 5.53 | Me | H | Me | H | CF₃ | CH | |
| 5.54 | Me | OH | H | Me | CF₃ | CH | |
| 5.55 | Me | Me | H | H | CF₃ | CH | |
| 5.56 | Me | OMe | H | H | CF₃ | CH | |
| 5.57 | Me | H | H | H | Cl | N | |
| 5.58 | Me | H | H | H | Cl | CH | |
| 5.59 | Me | H | H | H | Cl | CMe | |
| 5.60 | Me | H | H | H | Cl | CCl | |
| 5.61 | Me | H | Me | H | Cl | CH | |
| 5.62 | Me | OH | H | Me | Cl | CH | |

TABLE 5-continued

Compounds of the formula (I) according to the invention in which the substituents and symbols are defined as follows:

Y = Y4   $R^6$ = H   $R^7$ = Me

| No. | $R^1$ | $R^2$ | $R^3$ | $R^4$ | $R^5$ | Z | Physical Data |
|---|---|---|---|---|---|---|---|
| 5.63 | Me | Me | H | H | Cl | CH | |
| 5.64 | Me | OMe | H | H | Cl | CH | |
| 5.65 | Me | H | H | H | CN | N | |
| 5.66 | Me | H | H | H | CN | CH | |
| 5.67 | Me | H | H | H | CN | CMe | |
| 5.68 | Me | H | H | H | CN | CCl | |
| 5.69 | Me | H | Me | H | CN | CH | |
| 5.70 | Me | OH | H | Me | CN | CH | |
| 5.71 | Me | Me | H | H | CN | CH | |
| 5.72 | Me | OMe | H | H | CN | CH | |
| 5.73 | Me | H | H | H | $OCF_2H$ | N | |
| 5.74 | Me | H | H | H | $OCF_2H$ | CH | |
| 5.75 | Me | H | H | H | $OCF_2H$ | CMe | |
| 5.76 | Me | H | H | H | $OCF_2H$ | CCl | |
| 5.77 | Me | H | Me | H | $OCF_2H$ | CH | |
| 5.78 | Me | OH | H | Me | $OCF_2H$ | CH | |
| 5.79 | Me | Me | H | H | $OCF_2H$ | CH | |
| 5.80 | Me | OMe | H | H | $OCF_2H$ | CH | |
| 5.81 | Me | H | H | H | CN | N | |
| 5.82 | Me | H | H | H | CN | CH | |
| 5.83 | Me | H | H | H | CN | CMe | |
| 5.84 | Me | H | H | H | CN | CCl | |
| 5.85 | Me | H | Me | H | CN | CH | |
| 5.86 | Me | OH | H | Me | CN | CH | |
| 5.87 | Me | Me | H | H | CN | CH | |
| 5.88 | Me | OMe | H | H | CN | CH | |
| 5.89 | Me | H | H | H | CN | N | |
| 5.90 | Me | H | H | H | CN | CH | |
| 5.91 | Me | H | H | H | CN | CMe | |
| 5.92 | Me | H | H | H | CN | CCl | |
| 5.93 | Me | H | Me | H | CN | CH | |
| 5.94 | Me | OH | H | Me | CN | CH | |
| 5.95 | Me | Me | H | H | CN | CH | |
| 5.96 | Me | OMe | H | H | CN | CH | |
| 5.97 | CN | H | H | H | $CF_3$ | N | |
| 5.98 | CN | H | H | H | $CF_3$ | CH | |
| 5.99 | CN | H | H | H | $CF_3$ | CMe | |
| 5.100 | CN | H | H | H | $CF_3$ | CCl | |
| 5.101 | CN | H | Me | H | $CF_3$ | CH | |
| 5.102 | CN | OH | H | Me | $CF_3$ | CH | |
| 5.103 | CN | Me | H | H | $CF_3$ | CH | |
| 5.104 | CN | OMe | H | H | $CF_3$ | CH | |
| 5.105 | CN | H | H | H | Cl | N | |
| 5.106 | CN | H | H | H | Cl | CH | |
| 5.107 | CN | H | H | H | Cl | CMe | |
| 5.108 | CN | H | H | H | Cl | CCl | |
| 5.109 | CN | H | Me | H | Cl | CH | |
| 5.110 | CN | OH | H | Me | Cl | CH | |
| 5.111 | CN | Me | H | H | Cl | CH | |
| 5.112 | CN | OMe | H | H | Cl | CH | |
| 5.113 | CN | H | H | H | CN | N | |
| 5.114 | CN | H | H | H | CN | CH | |
| 5.115 | CN | H | H | H | CN | CMe | |
| 5.116 | CN | H | H | H | CN | CCl | |
| 5.117 | CN | H | Me | H | CN | CH | |
| 5.118 | CN | OH | H | Me | CN | CH | |
| 5.119 | CN | Me | H | H | CN | CH | |
| 5.120 | CN | OMe | H | H | CN | CH | |
| 5.121 | CN | H | H | H | $OCF_2H$ | N | |
| 5.122 | CN | H | H | H | $OCF_2H$ | CH | |
| 5.123 | CN | H | H | H | $OCF_2H$ | CMe | |
| 5.124 | CN | H | H | H | $OCF_2H$ | CCl | |
| 5.125 | CN | H | Me | H | $OCF_2H$ | CH | |
| 5.126 | CN | OH | H | Me | $OCF_2H$ | CH | |
| 5.127 | CN | Me | H | H | $OCF_2H$ | CH | |
| 5.128 | CN | OMe | H | H | $OCF_2H$ | CH | |
| 5.129 | CN | H | H | H | CN | N | |
| 5.130 | CN | H | H | H | CN | CH | |
| 5.131 | CN | H | H | H | CN | CMe | |
| 5.132 | CN | H | H | H | CN | CCl | |
| 5.133 | CN | H | Me | H | CN | CH | |
| 5.134 | CN | OH | H | Me | CN | CH | |
| 5.135 | CN | Me | H | H | CN | CH | |
| 5.136 | CN | OMe | H | H | CN | CH | |
| 5.137 | CN | H | H | H | CN | N | |
| 5.138 | CN | H | H | H | CN | CH | |
| 5.139 | CN | H | H | H | CN | CMe | |
| 5.140 | CN | H | H | H | CN | CCl | |
| 5.141 | CN | H | Me | H | CN | CH | |
| 5.142 | CN | OH | H | Me | CN | CH | |
| 5.143 | CN | Me | H | H | CN | CH | |
| 5.144 | CN | OMe | H | H | CN | CH | |
| 5.145 | OMe | H | H | H | $CF_3$ | N | |
| 5.146 | OMe | H | H | H | $CF_3$ | CH | |
| 5.147 | OMe | H | H | H | $CF_3$ | CMe | |
| 5.148 | OMe | H | H | H | $CF_3$ | CCl | |
| 5.149 | OMe | H | Me | H | $CF_3$ | CH | |
| 5.150 | OMe | OH | H | Me | $CF_3$ | CH | |
| 5.151 | OMe | Me | H | H | $CF_3$ | CH | |
| 5.152 | OMe | OMe | H | H | $CF_3$ | CH | |
| 5.153 | OMe | H | H | H | Cl | N | |
| 5.154 | OMe | H | H | H | Cl | CH | |
| 5.155 | OMe | H | H | H | Cl | CMe | |
| 5.156 | OMe | H | H | H | Cl | CCl | |
| 5.157 | OMe | H | Me | H | Cl | CH | |
| 5.158 | OMe | OH | H | Me | Cl | CH | |
| 5.159 | OMe | Me | H | H | Cl | CH | |
| 5.160 | OMe | OMe | H | H | Cl | CH | |
| 5.161 | OMe | H | H | H | CN | N | |
| 5.162 | OMe | H | H | H | CN | CH | |
| 5.163 | OMe | H | H | H | CN | CMe | |
| 5.164 | OMe | H | H | H | CN | CCl | |
| 5.165 | OMe | H | Me | H | CN | CH | |
| 5.166 | OMe | OH | H | Me | CN | CH | |
| 5.167 | OMe | Me | H | H | CN | CH | |
| 5.168 | OMe | OMe | H | H | CN | CH | |
| 5.169 | OMe | H | H | H | $OCF_2H$ | N | |
| 5.170 | OMe | H | H | H | $OCF_2H$ | CH | |
| 5.171 | OMe | H | H | H | $OCF_2H$ | CMe | |
| 5.172 | OMe | H | H | H | $OCF_2H$ | CCl | |
| 5.173 | OMe | H | Me | H | $OCF_2H$ | CH | |
| 5.174 | OMe | OH | H | Me | $OCF_2H$ | CH | |
| 5.175 | OMe | Me | H | H | $OCF_2H$ | CH | |
| 5.176 | OMe | OMe | H | H | $OCF_2H$ | CH | |
| 5.177 | OMe | H | H | H | CN | N | |
| 5.178 | OMe | H | H | H | CN | CH | |
| 5.179 | OMe | H | H | H | CN | CMe | |
| 5.180 | OMe | H | H | H | CN | CCl | |

TABLE 5-continued

Compounds of the formula (I) according to the invention in which the substituents and symbols are defined as follows:

Y = Y4   $R^6$ = H   $R^7$ = Me

| No. | $R^1$ | $R^2$ | $R^3$ | $R^4$ | $R^5$ | Z | Physical Data |
|---|---|---|---|---|---|---|---|
| 5.181 | OMe | H | Me | H | CN | CH | |
| 5.182 | OMe | OH | H | Me | CN | CH | |
| 5.183 | OMe | Me | H | H | CN | CH | |
| 5.184 | OMe | OMe | H | H | CN | CH | |
| 5.185 | OMe | H | H | H | CN | N | |
| 5.186 | OMe | H | H | H | CN | CH | |
| 5.187 | OMe | H | H | H | CN | CMe | |
| 5.188 | OMe | H | H | H | CN | CCl | |
| 5.189 | OMe | H | Me | H | CN | CH | |
| 5.190 | OMe | OH | H | Me | CN | CH | |
| 5.191 | OMe | Me | H | H | CN | CH | |
| 5.192 | OMe | OMe | H | H | CN | CH | |

TABLE 6

Compounds of the formula (I) according to the invention in which the substituents and symbols are defined as follows:

Y = Y6   $R^6$ = H   $R^7$ = Me

| No. | $R^1$ | $R^2$ | $R^3$ | $R^4$ | $R^5$ | Z | Physical Data |
|---|---|---|---|---|---|---|---|
| 6.1 | H | H | H | H | $CF_3$ | N | |
| 6.2 | H | H | H | H | $CF_3$ | CH | |
| 6.3 | H | H | H | H | $CF_3$ | CMe | |
| 6.4 | H | H | H | H | $CF_3$ | CCl | |
| 6.5 | H | H | Me | H | $CF_3$ | CH | |
| 6.6 | H | OH | H | Me | $CF_3$ | CH | |
| 6.7 | H | Me | H | H | $CF_3$ | CH | |
| 6.8 | H | OMe | H | H | $CF_3$ | CH | |
| 6.9 | H | H | H | H | Cl | N | |
| 6.10 | H | H | H | H | Cl | CH | |
| 6.11 | H | H | H | H | Cl | CMe | |
| 6.12 | H | H | H | H | Cl | CCl | |
| 6.13 | H | H | Me | H | Cl | CH | |
| 6.14 | H | OH | H | Me | Cl | CH | |
| 6.15 | H | Me | H | H | Cl | CH | |
| 6.16 | H | OMe | H | H | Cl | CH | |
| 6.17 | H | H | H | H | CN | N | |
| 6.18 | H | H | H | H | CN | CH | |
| 6.19 | H | H | H | H | CN | CMe | |
| 6.20 | H | H | H | H | CN | CCl | |
| 6.21 | H | H | Me | H | CN | CH | |
| 6.22 | H | OH | H | Me | CN | CH | |
| 6.23 | H | Me | H | H | CN | CH | |

TABLE 6-continued

Compounds of the formula (I) according to the invention in which the substituents and symbols are defined as follows:

Y = Y6   $R^6$ = H   $R^7$ = Me

| No. | $R^1$ | $R^2$ | $R^3$ | $R^4$ | $R^5$ | Z | Physical Data |
|---|---|---|---|---|---|---|---|
| 6.24 | H | OMe | H | H | CN | CH | |
| 6.25 | H | H | H | H | $OCF_2H$ | N | |
| 6.26 | H | H | H | H | $OCF_2H$ | CH | |
| 6.27 | H | H | H | H | $OCF_2H$ | CMe | |
| 6.28 | H | H | H | H | $OCF_2H$ | CCl | |
| 6.29 | H | H | Me | H | $OCF_2H$ | CH | |
| 6.30 | H | OH | H | Me | $OCF_2H$ | CH | |
| 6.31 | H | Me | H | H | $OCF_2H$ | CH | |
| 6.32 | H | OMe | H | H | $OCF_2H$ | CH | |
| 6.33 | H | H | H | H | CN | N | |
| 6.34 | H | H | H | H | CN | CH | |
| 6.35 | H | H | H | H | CN | CMe | |
| 6.36 | H | H | H | H | CN | CCl | |
| 6.37 | H | H | Me | H | CN | CH | |
| 6.38 | H | OH | H | Me | CN | CH | |
| 6.39 | H | Me | H | H | CN | CH | |
| 6.40 | H | OMe | H | H | CN | CH | |
| 6.41 | H | H | H | H | CN | N | |
| 6.42 | H | H | H | H | CN | CH | |
| 6.43 | H | H | H | H | CN | CMe | |
| 6.44 | H | H | H | H | CN | CCl | |
| 6.45 | H | H | Me | H | CN | CH | |
| 6.46 | H | OH | H | Me | CN | CH | |
| 6.47 | H | Me | H | H | CN | CH | |
| 6.48 | H | OMe | H | H | CN | CH | |
| 6.49 | Me | H | H | H | $CF_3$ | N | |
| 6.50 | Me | H | H | H | $CF_3$ | CH | |
| 6.51 | Me | H | H | H | $CF_3$ | CMe | |
| 6.52 | Me | H | H | H | $CF_3$ | CCl | |
| 6.53 | Me | H | Me | H | $CF_3$ | CH | |
| 6.54 | Me | OH | H | Me | $CF_3$ | CH | |
| 6.55 | Me | Me | H | H | $CF_3$ | CH | |
| 6.56 | Me | OMe | H | H | $CF_3$ | CH | |
| 6.57 | Me | H | H | H | Cl | N | |
| 6.58 | Me | H | H | H | Cl | CH | |
| 6.59 | Me | H | H | H | Cl | CMe | |
| 6.60 | Me | H | H | H | Cl | CCl | |
| 6.61 | Me | H | Me | H | Cl | CH | |
| 6.62 | Me | OH | H | Me | Cl | CH | |
| 6.63 | Me | Me | H | H | Cl | CH | |
| 6.64 | Me | OMe | H | H | Cl | CH | |
| 6.65 | Me | H | H | H | CN | N | |
| 6.66 | Me | H | H | H | CN | CH | |
| 6.67 | Me | H | H | H | CN | CMe | |
| 6.68 | Me | H | H | H | CN | CCl | |
| 6.69 | Me | H | Me | H | CN | CH | |
| 6.70 | Me | OH | H | Me | CN | CH | |
| 6.71 | Me | Me | H | H | CN | CH | |
| 6.72 | Me | OMe | H | H | CN | CH | |
| 6.73 | Me | H | H | H | $OCF_2H$ | N | |
| 6.74 | Me | H | H | H | $OCF_2H$ | CH | |
| 6.75 | Me | H | H | H | $OCF_2H$ | CMe | |
| 6.76 | Me | H | H | H | $OCF_2H$ | CCl | |
| 6.77 | Me | H | Me | H | $OCF_2H$ | CH | |
| 6.78 | Me | OH | H | Me | $OCF_2H$ | CH | |
| 6.79 | Me | Me | H | H | $OCF_2H$ | CH | |
| 6.80 | Me | OMe | H | H | $OCF_2H$ | CH | |
| 6.81 | Me | H | H | H | CN | N | |
| 6.82 | Me | H | H | H | CN | CH | |

TABLE 6-continued

Compounds of the formula (I) according to the invention in which the substituents and symbols are defined as follows:

Y = Y6   R⁶ = H   R⁷ = Me

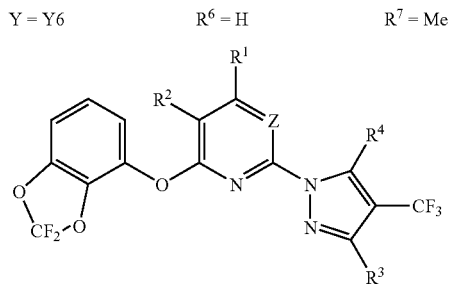

| No. | R¹ | R² | R³ | R⁴ | R⁵ | Z | Physical Data |
|---|---|---|---|---|---|---|---|
| 6.83 | Me | H | H | H | CN | CMe | |
| 6.84 | Me | H | H | H | CN | CCl | |
| 6.85 | Me | H | Me | H | CN | CH | |
| 6.86 | Me | OH | H | Me | CN | CH | |
| 6.87 | Me | Me | H | H | CN | CH | |
| 6.88 | Me | OMe | H | H | CN | CH | |
| 6.89 | Me | H | H | H | CN | N | |
| 6.90 | Me | H | H | H | CN | CH | |
| 6.91 | Me | H | H | H | CN | CMe | |
| 6.92 | Me | H | H | H | CN | CCl | |
| 6.93 | Me | H | Me | H | CN | CH | |
| 6.94 | Me | OH | H | Me | CN | CH | |
| 6.95 | Me | Me | H | H | CN | CH | |
| 6.96 | Me | OMe | H | H | CN | CH | |
| 6.97 | CN | H | H | H | CF₃ | N | |
| 6.98 | CN | H | H | H | CF₃ | CH | |
| 6.99 | CN | H | H | H | CF₃ | CMe | |
| 6.100 | CN | H | H | H | CF₃ | CCl | |
| 6.101 | CN | H | Me | H | CF₃ | CH | |
| 6.102 | CN | OH | H | Me | CF₃ | CH | |
| 6.103 | CN | Me | H | H | CF₃ | CH | |
| 6.104 | CN | OMe | H | H | CF₃ | CH | |
| 6.105 | CN | H | H | H | Cl | N | |
| 6.106 | CN | H | H | H | Cl | CH | |
| 6.107 | CN | H | H | H | Cl | CMe | |
| 6.108 | CN | H | H | H | Cl | CCl | |
| 6.109 | CN | H | Me | H | Cl | CH | |
| 6.110 | CN | OH | H | Me | Cl | CH | |
| 6.111 | CN | Me | H | H | Cl | CH | |
| 6.112 | CN | OMe | H | H | Cl | CH | |
| 6.113 | CN | H | H | H | CN | N | |
| 6.114 | CN | H | H | H | CN | CH | |
| 6.115 | CN | H | H | H | CN | CMe | |
| 6.116 | CN | H | H | H | CN | CCl | |
| 6.117 | CN | H | Me | H | CN | CH | |
| 6.118 | CN | OH | H | Me | CN | CH | |
| 6.119 | CN | Me | H | H | CN | CH | |
| 6.120 | CN | OMe | H | H | CN | CH | |
| 6.121 | CN | H | H | H | OCF₂H | N | |
| 6.122 | CN | H | H | H | OCF₂H | CH | |
| 6.123 | CN | H | H | H | OCF₂H | CMe | |
| 6.124 | CN | H | H | H | OCF₂H | CCl | |
| 6.125 | CN | H | Me | H | OCF₂H | CH | |
| 6.126 | CN | OH | H | Me | OCF₂H | CH | |
| 6.127 | CN | Me | H | H | OCF₂H | CH | |
| 6.128 | CN | OMe | H | H | OCF₂H | CH | |
| 6.129 | CN | H | H | H | CN | N | |
| 6.130 | CN | H | H | H | CN | CH | |
| 6.131 | CN | H | H | H | CN | CMe | |
| 6.132 | CN | H | H | H | CN | CCl | |
| 6.133 | CN | H | Me | H | CN | CH | |
| 6.134 | CN | OH | H | Me | CN | CH | |
| 6.135 | CN | Me | H | H | CN | CH | |
| 6.136 | CN | OMe | H | H | CN | CH | |
| 6.137 | CN | H | H | H | CN | N | |
| 6.138 | CN | H | H | H | CN | CH | |
| 6.139 | CN | H | H | H | CN | CMe | |
| 6.140 | CN | H | H | H | CN | CCl | |
| 6.141 | CN | H | Me | H | CN | CH | |
| 6.142 | CN | OH | H | Me | CN | CH | |
| 6.143 | CN | Me | H | H | CN | CH | |
| 6.144 | CN | OMe | H | H | CN | CH | |
| 6.145 | OMe | H | H | H | CF₃ | N | |
| 6.146 | OMe | H | H | H | CF₃ | CH | |
| 6.147 | OMe | H | H | H | CF₃ | CMe | |
| 6.148 | OMe | H | H | H | CF₃ | CCl | |
| 6.149 | OMe | H | Me | H | CF₃ | CH | |
| 6.150 | OMe | OH | H | Me | CF₃ | CH | |
| 6.151 | OMe | Me | H | H | CF₃ | CH | |
| 6.152 | OMe | OMe | H | H | CF₃ | CH | |
| 6.153 | OMe | H | H | H | Cl | N | |
| 6.154 | OMe | H | H | H | Cl | CH | |
| 6.155 | OMe | H | H | H | Cl | CMe | |
| 6.156 | OMe | H | H | H | Cl | CCl | |
| 6.157 | OMe | H | Me | H | Cl | CH | |
| 6.158 | OMe | OH | H | Me | Cl | CH | |
| 6.159 | OMe | Me | H | H | Cl | CH | |
| 6.160 | OMe | OMe | H | H | Cl | CH | |
| 6.161 | OMe | H | H | H | CN | N | |
| 6.162 | OMe | H | H | H | CN | CH | |
| 6.163 | OMe | H | H | H | CN | CMe | |
| 6.164 | OMe | H | H | H | CN | CCl | |
| 6.165 | OMe | H | Me | H | CN | CH | |
| 6.166 | OMe | OH | H | Me | CN | CH | |
| 6.167 | OMe | Me | H | H | CN | CH | |
| 6.168 | OMe | OMe | H | H | CN | CH | |
| 6.169 | OMe | H | H | H | OCF₂H | N | |
| 6.170 | OMe | H | H | H | OCF₂H | CH | |
| 6.171 | OMe | H | H | H | OCF₂H | CMe | |
| 6.172 | OMe | H | H | H | OCF₂H | CCl | |
| 6.173 | OMe | H | Me | H | OCF₂H | CH | |
| 6.174 | OMe | OH | H | Me | OCF₂H | CH | |
| 6.175 | OMe | Me | H | H | OCF₂H | CH | |
| 6.176 | OMe | OMe | H | H | OCF₂H | CH | |
| 6.177 | OMe | H | H | H | CN | N | |
| 6.178 | OMe | H | H | H | CN | CH | |
| 6.179 | OMe | H | H | H | CN | CMe | |
| 6.180 | OMe | H | H | H | CN | CCl | |
| 6.181 | OMe | H | Me | H | CN | CH | |
| 6.182 | OMe | OH | H | Me | CN | CH | |
| 6.183 | OMe | Me | H | H | CN | CH | |
| 6.184 | OMe | OMe | H | H | CN | CH | |
| 6.185 | OMe | H | H | H | CN | N | |
| 6.186 | OMe | H | H | H | CN | CH | |
| 6.187 | OMe | H | H | H | CN | CMe | |
| 6.188 | OMe | H | H | H | CN | CCl | |
| 6.189 | OMe | H | Me | H | CN | CH | |
| 6.190 | OMe | OH | H | Me | CN | CH | |
| 6.191 | OMe | Me | H | H | CN | CH | |
| 6.192 | OMe | OMe | H | H | CN | CH | |

B. FORMULATION EXAMPLES

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert material, 10 parts by weight of potassium ligninsulfonate and 1 part by weight of sodium oleoylmethyltauride as wetter and dispersant, and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (® Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-dispersible Granules

Water-dispersible granules are obtained by mixing 75 parts by weight of a compound of the formula (I),

| | |
|---|---|
| 10" | calcium ligninsulfonate, |
| 5" | sodium lauryl sulfate, |
| 3" | polyvinyl alcohol and |
| 7" | kaolin, | grinding the mixture in a pinned-disk mill and granulating the powder in a fluidized bed by spraying on water as granulation liquid.

Water-dispersible granules are also obtained by homogenizing and precomminuting, in a colloid mill, 25 parts by weight of a compound of the formula (I),

| | |
|---|---|
| 5" | sodium 2,2'-dinaphthylmethane-6,6'-disulfonate, |
| 2" | sodium oleoylmethyltauride, |
| 1" | polyvinyl alcohol, |
| 17" | calcium carbonate and |
| 50" | water, | subsequently grinding the mixture in a bead mill, and atomizing and drying the resulting suspension in a spray tower by means of a single-substance nozzle.

C. BIOLOGICAL EXAMPLES

1. Weed Plant Herbicidal Activity and Crop Plant Tolerance, Pre-emergence

Seeds of monocotyledonous and dicotyledonous weed plants and also of crop plants are placed in sandy loam soil in cardboard pots and are covered with soil. The compounds of the invention, formulated as wettable powders or emulsifiable concentrates, are then applied as an aqueous suspension or emulsion, respectively, and at different dosages to the surface of the covering soil at an application rate of 600 to 800 l of water per ha (converted). Following treatment, the pots are placed in a greenhouse and kept under good growth conditions for the weeds. Visual scoring of the plant damage or emergence damage is made after the test plants have emerged, after an experimental period of 3 to 4 weeks, in comparison with untreated controls. In this case, for example, the compounds of the invention from examples nos. 1.7 and 4.1 at a dosage of 320 g of active substance per hectare display a 100% activity against *Digitaria sanguinalis, Setaria viridis* and *Amaranthus retroflexus*. At the same dosage these compounds of the invention cause no damage to the crop plants *Oryza sativa* (rice) and *Glycine max* (soybean). The compound of the invention from example no. 1.7 at a dosage of 20 g of active substance per hectare displays an at least 90% activity against *Alopecurus myosuroides, Setaria viridis, Amaranthus retroflexus* and *Veronica persica*. At the same dosage this compound of the invention causes no damage to the crop plants *Oryza sativa* (rice), *Zea mays* (maize) and *Glycine max* (soybean). At a dosage of 320 g of active substance per hectare, the compound of the invention from example no. 4.146 displays a 100% activity against *Amaranthus retroflexus, Setaria viridis* and *Stellaria media*.

2. Weed Plant Herbicidal Activity and Crop Plant Tolerance, Post-emergence

Seeds of monocotyledonous and dicotyledonous weed plants and also of crop plants are placed in sandy loam in cardboard pots, covered with soil, and grown in a greenhouse under good growth conditions. Two to three weeks after sowing, the test plants are treated at the three-leaf stage. The compounds of the invention, formulated as wettable powders or as emulsifiable concentrates, are sprayed at various dosages onto the surface of the green parts of the plants at an application rate of 600 to 800 l of water/per ha (converted). After the test plants have stood for 3 to 4 weeks in a greenhouse under optimum growth conditions, the activity of the compounds is scored. In this case, for example, at a dosage of 80 g of active substance per hectare, the compounds of the invention from examples nos. 4.1 and 4.49 display an at least 90% activity against *Setaria viridis, Digitaria sanguinalis, Matricaria inodora, Amaranthus retroflexus, Pharbitis purpureum, Chenopodium album, Veronica persica* and *Abutilon theophrasti*.

What is claimed is:

1. A compound of the formula (I) or N-oxide or salt thereof,

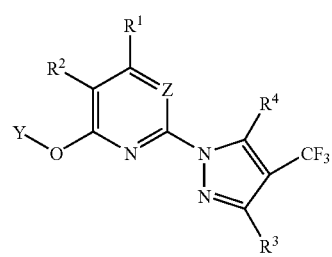

(I)

in which the radicals and indices have the following definitions:

Z is N or CR⁸;

Y is a radical from the group Y1 to Y7:

Y1
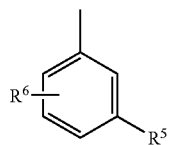

Y2
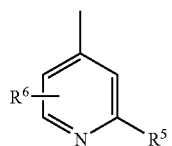

Y3
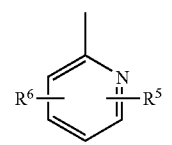

Y4
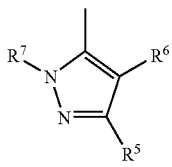

Y5
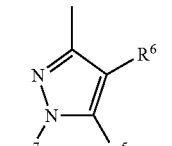

Y6
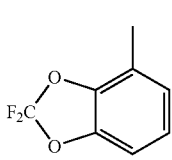

Y7
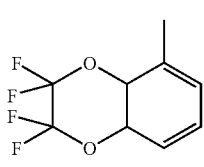

$R^1$ and $R^2$ independently are each hydrogen, halogen, cyano, isocyano, OH, COOR¹⁰, COR¹⁰, CH₂OH, CH₂SH, CH₂NH₂, NO₂, CSNH₂, CONH₂, (C₁-C₄)-alkyl, halo-(C₁-C₄-alkyl, (C₃-C₆)-cycloalkyl, (C₁-C₄)-alkoxy, halo-(C₁-C₄)-alkoxy, (C₁-C₂)-alkoxy-(C₁-C₂)-alkyl, (C₂-C₄)-alkenyl, (C₂-C₄)-alkynyl, (C₃-C₄)-alkenyloxy, (C₃-C₄)-alkynyloxy, (C₁-C₂)-alkylthio-(C₁-C₂)-alkyl, S(O)ₙR⁹, (C₁-C₂)-alkylsulfonyl-(C₁-C₂)-alkyl, amino, (C₁-C₄)-alkylamino, (C₁-C₃)-alkylcarbonylamino, (C₁-C₄)-alkylsulfonylamino or di-(C₁-C₄)-alkylamino;

$R^3$ and $R^4$ independently are each hydrogen, halogen, cyano, (C₁-C₄)-alkyl, halo-(C₁-C₄)-alkyl, (C₁-C₄)-alkoxy or halo-(C₁-C₄)-alkoxy;

$R^5$ is halogen, cyano, (C₁-C₄-alkyl, halo-(C₁-C₄)-alkyl, (C₁-C₄)-alkoxy, halo-(C₁)-C₄)-alkoxy, halo-(C₁-C₄)-alkylthio, (C₃-C₅)-cycloalkyl, halo-(C₃-C₅)-cycloalkyl, SF₅, S(O)ₙR⁹, (C₂-C₄)-alkenyl or (C₂-C₄)-alkynyl;

$R^6$ is hydrogen, halogen, cyano, (C₁-C₄)-alkyl, halo-(C₁-C₄)-alkyl, (C₁-C₄)-alkoxy, halo-(C₁-C₄)-alkoxy or S(O)ₙR⁹;

$R^7$ is (C₁-C₄)-alkyl;

$R^8$ is hydrogen, halogen, cyano, NO₂, (C₁-C₄)-alkyl, (C₁-C₄)-alkoxy, hydroxy, amino, (C₁-C₄)-alkylamino, (C₁-C₃)-alkylcarbonylamino, (C₁-C₄)-alkylsulfonylamino, di-(C₁-C₄)-alkylamino or S(O)ₙR⁹;

$R^9$ is hydrogen, (C₁-C₄)-alkyl or halo-(C₁-C₄)-alkyl;

$R^{10}$ is hydrogen or (C₁-C₄)-alkyl;

n is 0, 1 or 2.

2. A compound as claimed in claim 1, wherein Y is a radical from the group Y1 to Y6.

3. A compound as claimed in claim 1, wherein $R^1$ and $R^2$ independently are each hydrogen, halogen, cyano, OH, CHO, vinyl, (C₁-C₄)-alkyl, halo-(C₁-C₄)-alkyl, vinyl or (C₁-C₄)-alkoxy.

4. A compound as claimed in claim 1, wherein $R^3$ and $R^4$ independently are each hydrogen, halogen, methyl or methoxy.

5. A compound as claimed in claim 1, wherein
$R^1$ is hydrogen, halogen, cyano, CHO, methoxy, methyl or ethyl, and
$R^2$ is hydrogen, OH, methyl, ethyl, methoxy or ethoxy.

6. A compound as claimed in claim 1, wherein $R^3$ and $R^4$ are each hydrogen or methyl.

7. A compound as claimed in claim 1, wherein $R^8$ is hydrogen, halogen or (C₁-C₄)-alkyl.

8. A compound as claimed in claim 1, wherein $R^5$ is halogen, cyano, halo-(C₁-C₄)-alkyl, halo-(C₁-C₄)-alkoxy or halo-(C₁-C₄)-alkylthio.

9. A compound as claimed in claim 1, wherein $R^6$ is hydrogen.

10. A herbicidal composition comprising a herbicidally effective amount of at least one compound of the formula (I) as claimed in claim 1.

11. A herbicidal composition as claimed in claim 10 in a mixture with formulation auxiliaries.

12. A method of controlling unwanted plants, which comprises applying an effective amount of at least one compound of the formula (I) as claimed in claim 1 to the plants or to the site of the unwanted plant growth.

13. The method as claimed in claim 12, wherein the compound of the formula (I) is used to control unwanted plants in crops of useful plants.

14. The method as claimed in claim 13, wherein the useful plants are transgenic.

* * * * *